United States Patent
Geboers et al.

(10) Patent No.: US 8,622,241 B2
(45) Date of Patent: Jan. 7, 2014

(54) DISPENSER

(75) Inventors: Josephus Geboers, MA Valkenswaard (NL); Guy De Sevaux, Den Haag (NL); Jean-Pierre Giraud, Auburn (AL); Michel Zbirka, Jouy-sur-Morin (FR)

(73) Assignee: CSP Technologies, Inc., Amsterdam, NY (US)

( * ) Notice: Subject to any disclaimer, the term of this patent is extended or adjusted under 35 U.S.C. 154(b) by 218 days.

(21) Appl. No.: 13/139,073

(22) PCT Filed: Dec. 11, 2009

(86) PCT No.: PCT/EP2009/008898
§ 371 (c)(1),
(2), (4) Date: Sep. 22, 2011

(87) PCT Pub. No.: WO2010/066456
PCT Pub. Date: Jun. 17, 2010

(65) Prior Publication Data
US 2012/0006700 A1    Jan. 12, 2012

(30) Foreign Application Priority Data

Dec. 12, 2008  (EP) .................................... 08171568
Dec. 12, 2008  (EP) .................................... 08171578

(51) Int. Cl.
*A61J 1/03*  (2006.01)
(52) U.S. Cl.
USPC ........... 221/265; 221/264; 221/113; 206/539; 206/533
(58) Field of Classification Search
USPC .......... 221/112, 113, 263, 264, 265; 206/533, 206/538, 539
See application file for complete search history.

(56) References Cited

U.S. PATENT DOCUMENTS

| | | | | |
|---|---|---|---|---|
| 2,953,242 | A * | 9/1960 | Kinney | 206/534 |
| 4,127,190 | A * | 11/1978 | Sunnen | 206/535 |
| 4,174,034 | A | 11/1979 | Hoo | |
| 4,288,006 | A * | 9/1981 | Clover, Jr. | 222/42 |
| 4,572,376 | A * | 2/1986 | Wrennall | 206/538 |
| 4,583,661 | A * | 4/1986 | Clover, Jr. | 222/42 |
| 4,583,667 | A * | 4/1986 | Fishman et al. | 222/142.6 |
| 4,756,434 | A * | 7/1988 | Frank | 215/201 |
| 4,813,173 | A * | 3/1989 | Abbotoy | 43/57.1 |
| 5,310,082 | A | 5/1994 | Coustenoble | |
| 5,791,515 | A * | 8/1998 | Khan et al. | 221/154 |
| 6,478,155 | B2 * | 11/2002 | Bunyan | 206/538 |

(Continued)

OTHER PUBLICATIONS

European Patent Office, International Search Report in Application No. PCT/EP2009/008898, dated Mar. 23, 2010.
European Patent Office, Written Opinion of the International Searching Authority in Application No. PCT/EP2009/008898, dated Mar. 23, 2010.

(Continued)

*Primary Examiner* — Patrick MacKey
(74) *Attorney, Agent, or Firm* — McAndrews, Held & Malloy Ltd.

(57) ABSTRACT

For a dispenser (1) comprising the components of a reservoir (5) having a plurality of compartments (6), and a positioning disc (16) having a plurality of exit orifices (15), a solution shall be provided which allows realizing such a dispenser in a smaller sized configuration and which allows to dispense capsules or pills stored therein in a unit dose manner. This is achieved by additionally providing the component of a guiding member (56, 56*a*) being rotatably arranged in between the reservoir (5) and the positioning disc (16) and respectively connecting one compartment (6) with one dedicated exit orifice (15) in dispensing communication by accomplishing a rotary/rotational step.

17 Claims, 15 Drawing Sheets

(56) References Cited

U.S. PATENT DOCUMENTS

Figure 1:
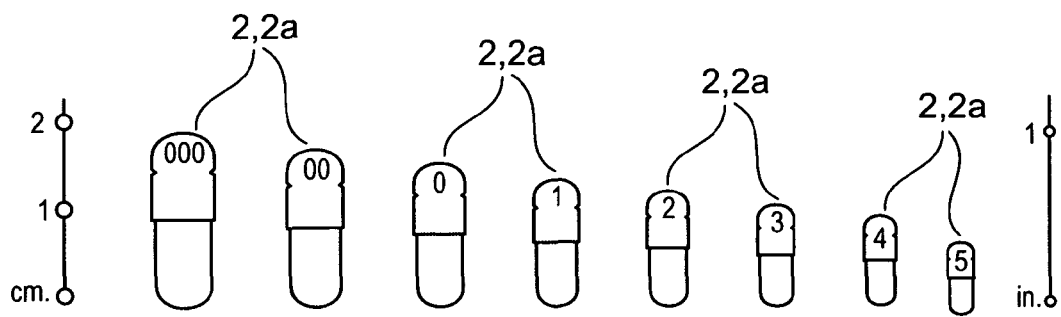

| | | | |
|---|---|---|---|
| 7,240,795 B2 * | 7/2007 | Lee | 206/539 |
| 2004/0154955 A1 * | 8/2004 | Friar et al. | 206/533 |
| 2009/0050514 A1 * | 2/2009 | Devaux-Day | 206/538 |
| 2009/0127157 A1 * | 5/2009 | Costa et al. | 206/534 |
| 2010/0206766 A1 * | 8/2010 | Warman | 206/538 |
| 2010/0300925 A1 * | 12/2010 | Kan | 206/534 |
| 2012/0248004 A1 * | 10/2012 | Naghavi et al. | 206/538 |

OTHER PUBLICATIONS

European Patent Office, International Preliminary Report on Patentability in Application No. PCT/EP2009/008898, dated Nov. 12, 2010.

State Intellectual Property Office of the People's Republic of China, Notification of First Office Action, in International application No. 200980149470.1, dated Jan. 14, 2013. (16 pages).

* cited by examiner

DISPENSER

The invention refers to a dispenser comprising the components of a reservoir having a plurality of compartments, and a positioning disc having a plurality of exit orifices, and a guiding member connecting one compartment with one dedicated exit orifice in dispensing communication.

It further refers to a dispenser comprising the components of a reservoir having a plurality of compartments and a positioning disc having at least one exit orifice, and a guiding member for respectively connecting one compartment with the at least one exit orifice, wherein at least one of these components is rotatably arranged in respect to the respective other components.

E.g., for a dispenser (1) comprising the components of a reservoir (5) having a plurality of compartments (6), and a positioning disc (16) having a plurality of exit orifices (15), a technical solution shall be provided which allows realizing such a dispenser in a smaller sized configuration and which allows to dispense capsules or pills stored therein in a unit dose manner. This is achieved by additionally providing the component of a guiding member (56, 56a) being rotatably arranged in between the reservoir (5) and the positioning disc (16) and respectively connecting one compartment (6) with one dedicated exit orifice (15) in dispensing communication by accomplishing a rotary/rotational step.

There is a need for a dispensing device, especially one which is able to dose only a single dose even when the dispensing device contains a plurality of doses. There is a further need that such a dispensing device or dispenser can additionally capture, record and transmit the dispensing event to an external device. Such a device is a combination of a dispenser with electronics, communication software and a database management system. These devices aim at improving the compliance of patients to their medication prescription and the medication that patients take every day is measured by electronics in the dispenser. Such a unit dose dispenser can be used for:

Clinical Trials, wherein the unit dose dispenser can be used to more accurately record information about patient compliance in taking medication. The compliance data can also be integrated with other diagnostic testing to provide integrated data on each patient for the clinical trial. Such a dispenser can be used by companies that manage clinical trials—accurate data collection with less labor.

Prescriptions for Maintenance Drugs, wherein the unit dose dispenser can be used by pharmacist as a compliance tool. After patient takes the prescription, the dispenser is returned to the Pharmacy where data is downloaded to a database. Pharmacist can evaluate compliance and coach behavior on how to take prescription (if necessary). Pharmacist can also share data from the unit dose dispenser with the prescribing physician.

Hospital, Nursing Home, Assisted Living, wherein the dispenser may contribute to improve compliance and more efficiency dispense medication.

There is a further need to provide medication delivery systems that improve the ease of living of patients who are on complex prescription regimes. At present, such patients may have to stay at home to have access to their medications, and to the reminders and alerts to take their various medications. Even when electronics systems have been used to provide such reminders and record compliance data, they have generally required a physical connection (such as through a USB reader) to a communication system to report compliance data and receive schedules for taking medication. In many instances, special purpose devices are required to communicate with medication dispensers, increasing the burden for patients who travel.

U.S. Pat. No. 2,953,242 shows a container and time indicator, by means of which filled compartments can be emptied completely at once. Hence, it does not describe a dispenser which is able to dispense single dose units from a plurality of single dose units, e.g. capsules or pills.

U.S. Pat. No. 4,572,376 shows a dial pill box comprising a container with several storage compartments, a pair of lids and a central pivot pin to pivotably hold together these parts.

A dispenser apparatus of this type to be used in the field of monitoring the taking of medications by a user is known from the U.S. Pat. No. 5,310,082 A. This document discloses a dispenser apparatus for medications in capsule or pill form which includes a main housing dispensing the medication and removable loader or capsule reservoir capable of containing the medications previously put into the loader or reservoir. The housing includes an indexing mechanism for rotating the dispenser in a given direction over a discrete compartment in the reservoir, and optical detection arranged in order to detect the passage of a medication at the moment of its exit from the indexing mechanism through a capsule positioning disc, which optical detection is connected to an electronic device for storing, computing and retrieving the data relating to the dispensing for medications, which electronic device is arranged on an electronics disc. The reservoir includes several transverse compartments, each forming a continuous longitudinal chain, the reservoir and the exit orifice being arranged in order to allow the exit of the medication directly under gravity when it is dispensed. The housing further includes a driving and indexing wheel driving the positioning wheel to align one single compartment with the exit orifice and interacting with an actuator.

Due to the fact that the reservoir is in the form of a continuous longitudinal chain comprising a series of compartments it is necessary to move the whole chain to align a compartment with the exit orifice. This makes it necessary to have a housing that provides enough space to store and move the chain, which needs the housing to be of some remarkable size. Additionally, the chain has to be flexible which provides some problems in respect to the interaction between a toothed indexing wheel and the chain, because each compartment has to be fetched between two adjacent teeth. Therefore, it is a disadvantage of the known dispenser that both, the indexing wheel and the reservoir have to be moved in order to align a compartment of the reservoir with an exit orifice of the dispenser.

It is an object of the present invention to provide a solution which allows realizing a generic dispenser in a smaller sized configuration. It is a further object of the invention to provide a dispenser which is suited to dispense capsules or pills stored therein in a unit dose manner (unit dose dispenser).

According to a first aspect of the invention this object is reached by a dispenser comprising the components of
a reservoir having a plurality of compartments, and
a positioning disc having a plurality of exit orifices, and
a guiding member being rotatably arranged in between the reservoir and the positioning disc and respectively connecting one compartment with one dedicated exit orifice in dispensing communication by accomplishing a rotary/rotational step.

Also, according to a second aspect of the invention, this object is reached by a dispenser comprising the components of
a reservoir having a plurality of compartments, and
a positioning disc having at least one exit orifice, and a guiding member for respectively connecting one compartment with the at least one exit orifice, wherein at least one of these components is rotatably arranged in respect to the respective other components, and comprising an actuator shaped and arranged for releasably assuring a stoppage of the at least one rotatably arranged component when the at least one rotatably arranged component accomplishes a rotary/rotational step to bring a compartment of the reservoir in dispensing communication with the at least one exit orifice.

In a preferred embodiment of the invention the dispensers of the above mentioned aspects are dispensers for dispensing in a unit dose manner.

This unit dose manner dispension will be explained in detail below.

In another preferred embodiment of the invention, the dispensers are dispensers for dispensing solid preparations having the spatial dimensions of a capsule or pill.

In another preferred embodiment, the dispensers are dispensers for dispensing solid preparations having the spatial dimensions of a capsule or pill from a plurality of compartments respectively comprising a plurality of solid preparations having the spatial dimensions of a capsule or pill, preferably in a unit dose manner.

In another preferred embodiment of the invention the dispensers of the above mentioned aspects are dispensers for dispensing capsules or pills in a unit dose manner out of a plurality of compartments respectively comprising a plurality of pills or capsules.

The term "dispensing in a unit dose manner" may be understood in the context of the invention as an emptying process of the compartments which is performed by the dispenser unit dose by unit dose i.e. for example pill by pill, wherein simultaneously the respective rests of the pluralities of e.g. pills remain within the respective compartment. The respective rests may be extracted, released or dispensed from the respective compartments by the dispenser at a later point of time e.g. after one ore more rotary/rotational steps have been accomplished.

It shall be noted that the above and following examples that are described in the context of a substance, capsule or pill shall explicitly be understood as being also applicable for pharmaceutical, nutritional or confectionary dosage forms in general, and solid preparations in particular, like pills, capsules, tablets, granulate, dragees or the like, or other matter that is to be dispensed; solid preparations having the spatial dimensions of a capsule or pill, e.g. the size and/or shape of a capsule or pill, in particular capsules and pills themselves being preferred.

Advantageous and useful embodiments are provided by the dependent claims.

Due to the invention it is possible to build a dispenser or dispensing apparatus of smaller size compared to those of the prior art. Further, it is possible now to have only one of the components indexing wheel and reservoir to rotate relatively to the other, but it is not necessary anymore to have both components constructed to be rotatable. This additionally gives the possibility to build a reservoir having a lot of single compartments arranged at a relatively small base forming disc. Furthermore it is possible to build single compartments of the reservoir in greater dimension compared to the prior art, because the reservoir has not to rotate anymore, which makes it possible to increase the mass of the reservoir without influencing the functionality of the dispenser in a negative way. Thus, it is possible to provide single compartments each being able to store 1-10, or even more, capsules or pills. In a preferred embodiment, at least one, two or more, or all of the compartments are able to store a plurality of capsules or pills, i.e. at least 2 capsules or pills per compartment.

Because it is one aspect of the invention to provide a unit dose dispenser for dispensing pharmaceutical, nutritional or confectionary capsules or pills the embodiments of the invention comprise a driving mechanism and an actuator for releasable locking—and later on also unlocking again—driving means to stop further rotary motion when an index position for dispensing a single dose unit is reached and a single dispensing step is finished.

The dispenser for dispensing capsules or pills stored in a plurality of compartments in a unit dose manner thus allows to sequentially emptying the plurality of compartments each being filled with a plurality of capsules or pills in a unit dose manner. Thus a first single pill from a first compartment is extracted or released from the plurality of pills in the first compartment by accomplishing a first rotary/rotational step. Due to a second rotary/rotational step a second single pill from a second compartment is extracted or released from the plurality of pills in the second compartment and so on. The respective rest of the plurality of pills remains unreleased within the respective compartments and may be extracted or released during a subsequent round trip in a unit dose manner. This process is not limited to the amount of two compartments but may be also applied to any plurality of compartments.

After having completed a round trip from the first to the last compartment, a second round trip may be started. Thus the next single pill may be released. Therefore an arrangement of the compartments along a circumferential direction may be advantageous.

The dispensers of any of the above and following embodiments and aspects of the invention may be contained within a medication container.

Further the dispenser can incorporate electronics that detect when a capsule or a single dose unit of a substance is removed from the dispenser, records the event and transfers event information to an external device.

Preferably, the invention is a device for dispensing pharmaceutical capsules in a unit dose manner.

For this reason the dispenser in an advantageous embodiment discloses a dispenser, wherein the reservoir and the positioning disc comprise a correspondingly arranged number and configuration of compartments, each having an open end, and exit orifices, wherein the pattern of the open ends and the exit orifices are dislocated in respect to each other for some degrees in circumferential direction. This allows realizing a single unit dispensing by providing a driving mechanism which moves a guiding member by rotation to bring a substance or a capsule contained therein from a position communicating with an open end to a position communicating with an exit orifice by rotary/rotational movement driven by the driving mechanism.

An advantageous embodiment of the invention in respect to the first aspect comprises a dispenser with an actuator which is shaped and arranged for releasably assuring a stoppage of the rotatably arranged guiding member when the guiding member accomplishes the rotary/rotational step to bring a compartment of the reservoir in dispensing communication with one dedicated exit orifice.

An advantageous embodiment of the invention in respect to the second aspect comprises a dispenser, wherein the actuator and/or the guiding member are part of a driving mechanism which is releasably blocked by the actuator to stop further rotary/rotational motion when the driving mechanism reaches an index position indicating the dispensing communication.

Thereby the actuator is automatically moved during a rotary/rotational motion/rotational step into a blocking position due to its pivotable arrangement, which may be understood as a hingeable arrangement as will be described in more detail below.

In an advantageous embodiment, the actuator may be shaped and arranged to assure the stoppage or a blocking contact by interacting with a stopper member arranged at a component of the dispenser, e.g. a component of the dispenser selected from the group consisting of the reservoir, the positioning disc, the guiding member and a member at which the guiding member is arranged. In one embodiment of the dispenser the actuator may be shaped and arranged to assure the stoppage or a blocking contact by interacting with at least one stopper member arranged at one of the components of the reservoir and the positioning disc and the guiding member or at a member at which the guiding member is arranged.

Preferably according to the invention the guiding member constitutes a part of a rotatably arranged indexing wheel, so that it is easy to realise the rotary movement.

An advantageous arrangement of the actuator at the dispenser consists in that the actuator is pivotably connected to a rotatable member or a non-rotatable member, e.g. a rotatable or non-rotatable member of the dispenser wherein the member is selected from the group consisting of the reservoir, the positioning disc, the guiding member and the indexing wheel. Therefore, the invention further comprises a dispenser, wherein the actuator is pivotably arranged at one of the components of the reservoir and the positioning disc and the guiding member and the indexing wheel.

The terms "pivotably connected" and "pivotably arranged" may be understood in the context of the invention as comprising a hinge. In other words the actuator may be hingeably connected to and/or hingeably arranged at a rotatable member or a non-rotatable member of the dispenser.

The actuator may e.g. be arranged in such a way, that it carries out a rotation about one of its own axis in order to releasably assure a stoppage of the at least one rotatably arranged component when the at least one rotatably arranged component accomplishes a rotary/rotational step to bring a compartment of the reservoir in dispensing communication with the at least one exit orifice. Such a rotation is e.g. explained within the following description of FIG. 18.

In other words the actuator may be pivotably arranged at one of the components of the reservoir and the positioning disc and the guiding member and an indexing wheel in such a way, that during each accomplishment of a rotation/rotational step the actuator is automatically forced to move about this previously described axis to get from an unlocking into a locking position. Thus the pivotable arrangement of the actuator allows an automatic initiation of a movement of the actuator during accomplishing a rotary/rotational step.

In this aspect it is further of advantage when the guiding member and/or the indexing wheel are rotatably arranged at a housing and the reservoir and the positioning disc are non-rotatably arranged at the housing.

This can be realised by a dispenser, wherein the actuator comprises a stopper notch and a guiding notch, wherein the guiding notch interacts with one of the stopper members for carrying out a radially inwardly directed rotational movement of the stopper notch during each rotary/rotational step of the one rotatably arranged component of the reservoir and the positioning disc and the guiding member and the indexing wheel to bring the stopper notch into a blocking contact with another one, preferably an adjacently arranged one, of the stopper members afterwards for accomplishing the rotary/rotational step.

In this embodiment according to the invention it is advantageous if the stopper notch and the guiding notch are radially inwardly extending arranged at a horizontal member of the actuator which preferably is rotatably arranged at the indexing wheel.

Hereby can the number of stopper members correspond to the number of compartments.

The stopper members are provided at one of the non-rotatably arranged components of the reservoir and the positioning disc.

Furthermore the dispenser can provide a releasing member to cause the actuator to release the dispensing position and/or to pivot out of the stoppage or blocking contact with the respective stopper member. For this purpose the actuator may further comprise an actuator tab, preferably provided on the horizontal member, which interacts with the releasing member for pivoting the actuator back into a non-blocking position.

For storing a lot of substances, especially in form of capsules or pills, a dispenser may be provided, wherein the reservoir comprises a plurality of compartments, each of said compartments being capable of containing a substance therein and having at least one open end (10), and wherein the positioning disc comprises a corresponding number of exit orifices each being arranged at a longitudinal and/or vertical distance to the at least one open end of the respectively dedicated single compartment (6), and wherein the guiding member for guiding a substance from an open end of one compartment to the respective dedicated exit orifice comprises at least one dispensing opening and/or connecting channel, which can be positioned below the respective one open end by stepwise rotary/rotational movement of the indexing wheel to bring this respective open end in dispensing communication with the respective dedicated exit orifice for dispensing a unit dose of a substance contained in the respectively connected compartment by gravity.

For avoiding that a substance falls through the open ends of the compartments accidentally the indexing wheel comprises a substantially closed surface arranged to slide alongside the open ends of the compartments.

Further, the actuator may be connected to a rotatable member of the dispenser, especially the indexing wheel, for concurrent rotation and may comprise a stopper member, especially a stopper notch, for releasable engaging with a stopper element provided on a non-rotatable member of the dispenser, especially the positioning disc.

But alternatively it is also possible to provide a dispenser, wherein the actuator is connected to a non-rotatable member of the dispenser, especially the positioning disc, and comprises a stopper member for releasable engaging with a stopper element formed at a rotatable member of the dispenser, especially at the indexing wheel or a member connected thereto.

For housing all the elements the dispenser apparatus can be cylindrical-shaped and comprising a (main) housing, a cover, a capsule reservoir, an indexing wheel, and a capsule positioning disc. It can also be comprising an actuator and/or an electronics disc. The invention is therefore also characterized by a dispenser which is cylindrical-shaped and comprises the housing, a cover, the reservoir, especially sized to store and deliver capsules, the indexing wheel, and the positioning disc, and optionally the actuator and/or an electronics disc as additional components. A dispenser comprising the actuator as an additional component is a preferred embodiment. A dispenser comprising the electronics disc as an additional component is another preferred embodiment.

In order to provide an unlocking mechanism a dispenser apparatus may further comprise a cover which provides a releasing member, especially a ridge, which comes into a load transmitting contact with the actuator when the cover is seated on a housing and which moves the actuator out of its locked position engaging a stopper element. The invention therefore also provides a dispenser, wherein the cover provides the releasing member, especially in form of a ridge, which comes into a load transmitting contact with the actuator when the cover is seated on the housing and which moves the actuator out of its stoppage position engaging one of the stopper elements.

Thereby the actuator is able to perform such a movement which is initiated by the releasing member due to its pivotable arrangement. As a hinge function is provided by the actuator as described above and hereinafter the actuator can be forced to move out of its stoppage position by means of contacting the actuator with the releasing member.

Therefore the pivotable or hingeable arrangement of the actuator firstly allows an automatically initiated movement into a locking or stoppage position during a rotary/rotational step. Secondly it allows the releasing from this position by means of contacting the actuator with a cover that may comprise a releasing member in form of e.g. a ridge.

For providing a possibility for dispensing a single dose unit out of each compartment it is further advantageous when the indexing wheel rotates stepwise from one position to another to align a cylindrical reservoir compartment or tube with a receiving orifice of a guiding member and a dispensing orifice of the guiding member with an exit orifice, respectively, for dispensing a single dose of a substance or a capsule or a pill per each rotary step.

The dispenser apparatus may further comprise a sensor, especially being situated at a sensor mounting post of the actuator, detecting the dispensing of the substance or capsule from the dispenser. In this case it is of further advantage that the dispense event is stored and transmitted to an external device.

For carrying out a rotational motion the dispenser apparatus according to the invention can comprise a motor or solenoid and/or a motor driven spindle which interacts with the actuator to lock and/or unlock rotary/rotational movement of the at least one rotatably arranged component, preferably the indexing wheel.

The dispenser can be made unlocked by a motor driven spindle or solenoid that provides the motion necessary to unlock the dispensing mechanism. The motor or solenoid interacts with the actuator to lock and/or unlock the (capsule) dispenser.

One construction of such a kind may comprise a motor or solenoid and/or a motor driven spindle which moves the stopper notch, in its locking position engaging a stopper member and/or moves the stopper notch back from its locking position to its unlocked position where it is released from engaging one of the stopper members.

This may be supported by an external source so that the invention is further characterized in, that the dispenser receives commands, especially commands to lock and/or unlock the dispenser from an external source.

Further the cover and/or the main housing can be composed of a thermoplastic resin with good moisture barrier and structural properties. Preferred thermoplastics include polypropylene and polyethylene, wherein one special solution comprises that the cover and/or the main housing is overmoulded, wherein the respective outer surface is made of polypropylene or polyethylene and the respective inner surface is made of desiccant plastic. Thus, the invention is further characterized by a dispenser wherein at least one of the components of the reservoir and/or the positioning disc and/or the guiding member and/or the indexing wheel and/or the cover and/or the housing is composed of a polymer, especially a desiccant entrained polymer, preferably of polypropylene or polyethylene. It is further possible that the cover and/or the housing is overmoulded, wherein the outer surface is made of polypropylene or polyethylene and the inner surface is made of a desiccant entrained polymer.

The capsule reservoir may comprise a series of compartments or cylindrical tubes used to house one or more capsules per compartment or tube, wherein it finally is of advantage that the capsule reservoir is composed of polypropylene or polyethylene and/or of desiccant plastic.

The desiccant entrained polymer used for manufacturing the dispenser or components of it according to an embodiment of the present invention provides a polymer matrix within which a desiccant agent is entrained in the structure.

Desiccant agents may be anhydrous salts which tend to absorb water or moisture and form a stable salt or may be chemically reacting agents or may be physically absorbing agents. Any of these types may be employed within the polymer bases for the purposes of producing a desiccant entrained polymer. Suitable desiccating agents include silica gel, molecular sieve and naturally occurring clay compounds which would also include montmorillionite clay.

According to one further aspect of the invention the cover can form a moisture tight seal with the housing.

According to another aspect of the invention a dispenser can further comprise a transceiver for transmitting information on dispensing of capsules to an external device.

Further the transceiver can comprise a near field communication (NFC) transceiver.

Advantageously the transceiver further receives instructions for the dispenser.

It is further possible that the dispenser comprises a temperature sensor and/or humidity sensor and that the dispenser transmits information relating to a temperature and/or a humidity in the reservoir to an external device.

The dispenser can also comprise a temperature sensor, wherein the transceiver further transmits information relating to a temperature in the reservoir. Likewise the dispenser can additionally comprise a humidity sensor, wherein the transceiver further transmits information relating to a humidity in the reservoir.

Finally it is provided that the dispenser and/or the transceiver communicates with a second dispenser to coordinate the administration of medication from the (first) dispenser and the second dispenser.

According to another advantageous embodiment of the invention a dispenser is provided wherein the guiding member comprises a connecting channel, and wherein the connecting channel is of such a height that it can contain only one single dose unit, e.g. only one of the solid preparations having the spatial dimensions of a capsule or pill, e.g. of capsules or pills, stored in the compartments, which makes it possible to dispense one single dose unit during each rotary/rotational step.

Due to this embodiment and the provided mechanism it is possible to dispense one single dose unit during each rotary/rotational step of the guiding member or the component which is rotatably arranged within the dispenser. Furthermore a driving mechanism may be part of this embodiment which may carry out and control such a rotary/rotational stepwise motion or movement, even when a compartment contains more than one capsule or pill.

In other words the need to dispense only one pill or capsule from a respective plurality of pills or capsules out of a plurality of compartments is met with this exemplary embodiment of the invention. The dispenser makes it possible to selectively and sequentially dispense the stored solid preparation, e.g. pills or capsules in a unit dose manner.

According to another advantageous embodiment of the invention the previously described dispenser further comprises an indexing wheel, wherein the indexing wheel comprises the guiding member, wherein the indexing wheel comprises a receiving opening and a dispensing opening, and wherein the receiving opening and the dispensing opening are connected by the connecting channel.

This arrangement of the guiding member within the indexing wheel makes it possible to sequentially dispense exactly one single dose unit, e.g. one pill or capsule, by one rotary/rotational step from a plurality of different compartments. The indexing wheel may be used to initiate the corresponding rotation to release e.g. a first pill from a first compartment by a first rotation, and a second pill from a second compartment by a second rotation and so on. After one round trip, the dispension may start again from the first compartment.

According to another advantageous embodiment of the invention the previously described dispenser is provided wherein the receiving openings and the dispensing opening are of a double-hole pattern comprising two through holes and wherein the dispenser is adapted in such a way, that by accomplishing a rotary/rotational step only one of the through holes will be connected to an open end of a compartment, respectively, whereas the other one will simultaneously be connected to an exit orifice.

This process or mechanism which is provided by this exemplary embodiment of the invention will be explained hereinafter in more detail.

This mechanism permits the indexing wheel to rotate e.g. a single index position until a receiving hole or receiving opening of the indexing wheel is positioned at an open end of one of the compartments or cylindrical tubes of the capsule reservoir, which is situated above the receiving opening and a sliding surface. At the same time the opposing dispensing opening may be positioned above an exit orifice formed in a positioning disc. But, because the openings are of a double-hole pattern comprising two through holes, only one of the through holes will be connected to an open end of a compartment, respectively, whereas the other one will simultaneously be connected to an exit orifice. As the receiving opening and the dispensing opening are connected by a connecting channel these elements constitute a guiding member.

The positioning disc may have the same pattern of exit orifices as the reservoir and/or the base thereof has in respect to the pattern of open ends. But the positioning disc and the reservoir may be dislocated in respect to each other for some degrees in the circumferential direction. Therefore, a capsule or pill delivered or dispensed from one open end into the connecting channel can be transferred and moved to an exit orifice by the dispenser by rotary/rotational movement of the guiding member comprising the connecting channel.

Therefore, at each time the free cross section of each of the open ends is partly covered by a sectional material part of the positioning disc in case that one of the holes is aligned with an open end or is covered by the sliding surface of the indexing wheel. Due to this it is not possible for a capsule to fall straight from an open end through the receiving orifice, the dispensing opening and an exit orifice out of the dispenser.

For dispensing a capsule it may be necessary to rotate the guiding member or the rotatably arranged component in an e.g. clockwise direction by driving the indexing wheel such, that a through hole of the receiving opening is moved from a position being aligned with an open end to a position being aligned with an exit orifice, whereas simultaneously the respective other one of the through holes is moved from its position being aligned with an exit orifice to a position being aligned with one open end of a compartment of the reservoir.

Due to this mechanism a capsule may fall first into the connecting channel of the guiding member, but can not fall through due to the sectional material part of the positioning disc covering or crossing the free cross section of the respective through hole which is aligned with that compartment delivering a capsule at this moment.

Then the guiding member being formed as the connecting channel may be turned one rotary/rotational step by driving e.g. the indexing wheel until the respective through hole which contains a capsule is positioned above an exit orifice so that the capsule can fall out and leave the guiding member by gravity. Simultaneously the respective other one of the through holes has been moved during this same rotary/rotational step to a position to be aligned with one open end of one compartment now, so that it will receive a capsule now, which may be released by accomplishing a next rotary/rotational step.

According to another advantageous embodiment of the invention a dispenser according to one of the previously described embodiments is provided wherein the dispenser is arranged in such a way, that by accomplishing a rotary/rotational step a first pill or capsule is released from a first compartment into the guiding member and simultaneously a second pill or capsule from a second compartment is dispensed from the guiding member.

In other words the dispenser is adapted in such a way that by accomplishing a rotation of e.g. the guiding member which may e.g. be part of the index wheel, a gravity-induced falling movement of the first pill or capsule is initiated. This movement may be stopped by a gliding surface of the indexing wheel.

During a subsequent rotational step, which may be separated from the first step by a locking and unlocking step of the actuator, the pill or capsule is moved on and along this gliding surface towards an orifice. In other words it is pushed by the guiding member towards that orifice. This may be a translation of the pill. The final dispense event to the user happens when the pill or capsule arrives at that orifice and then falls out of the dispenser.

According to another advantageous embodiment of the invention a dispenser according to one of the previously described embodiments is provided wherein the dispenser is adapted in such a way that the non-rotatably arranged components of the reservoir, the positioning disc and the guiding member are non-rotatably arranged or fixed at the dispenser.

In other words only one of the components rotates and the other ones are fixed or stay stationary compared to the rotatably arranged component like e.g. the guiding member.

According to another aspect of the invention the use of a dispenser according to one of the preceding and following embodiments is provided for the dispension of a solid preparation having the spatial dimensions of a capsule or pill in a unit dose manner.

According to an exemplary embodiment of the previously described aspect the dispension is done out of a plurality of compartments respectively comprising a plurality of solid preparations having the spatial dimensions of a capsule or pill, e.g. a plurality of pills or capsules.

It has to be noted that some of the embodiments of the invention are described with reference to different subject-matters. In particular, some embodiments are described with reference to apparatus type subject-matter whereas other embodiments are described with reference to use or method type subject-matter. However, a person skilled in the art will gather from the above and the following description that unless other notified in addition to any combination of features belonging to one type of subject-matter also any combination between features relating to different subject-matters is considered to be disclosed with this application.

Figure 2:
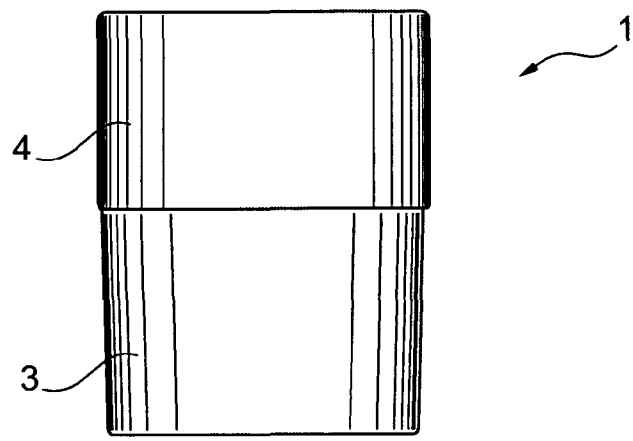
Figure 3:
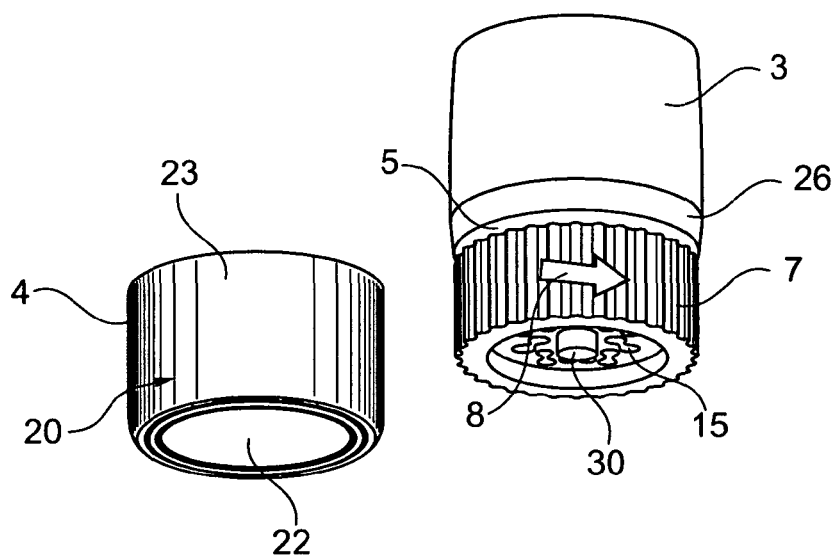
Figure 4:
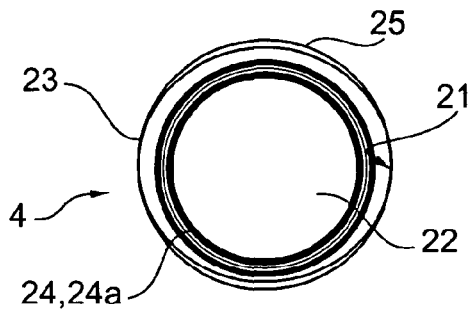
Figure 5:
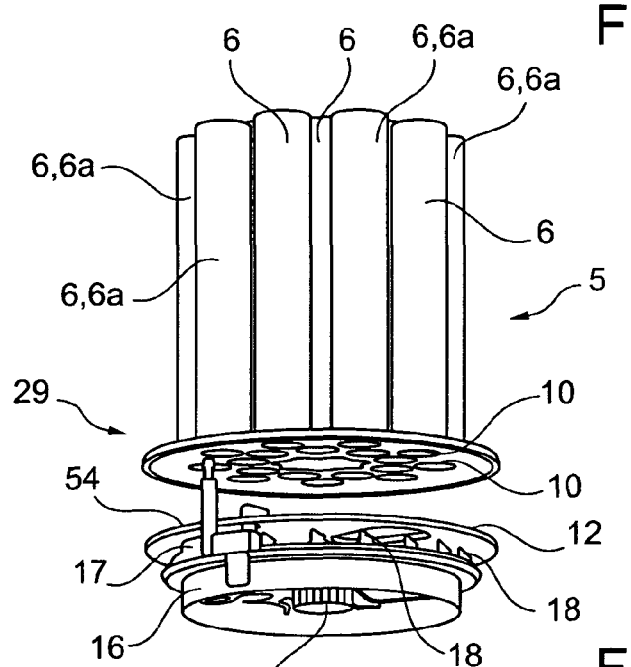
Figure 6:
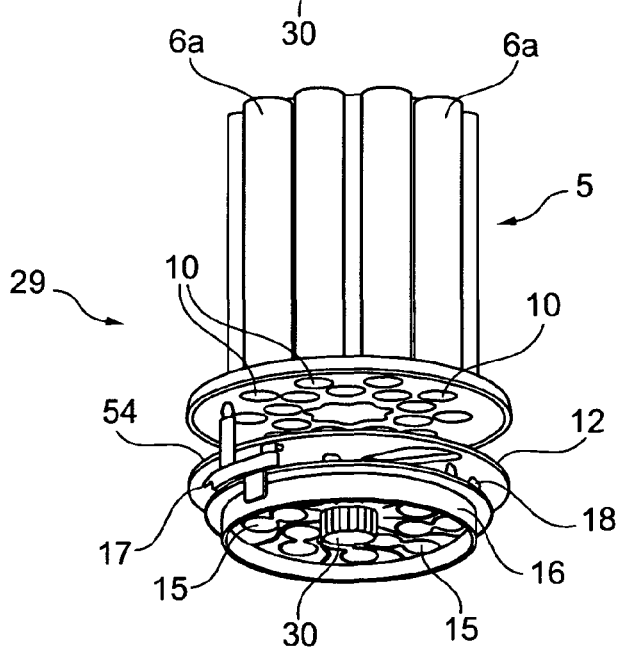
Figure 7:
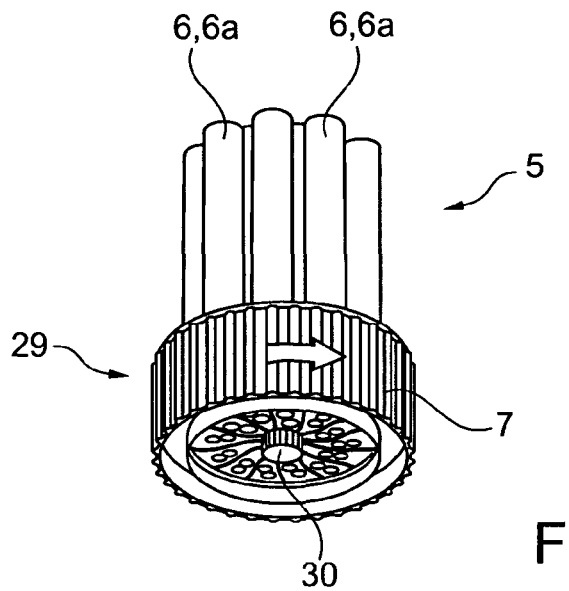
Figure 8:
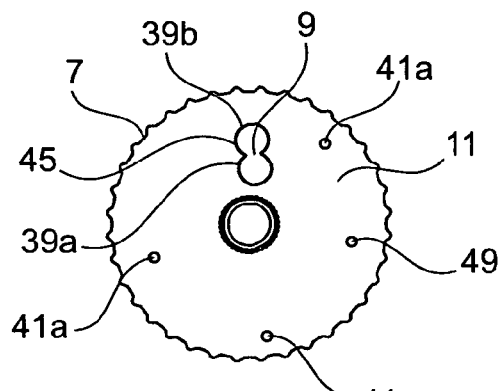
Figure 9:
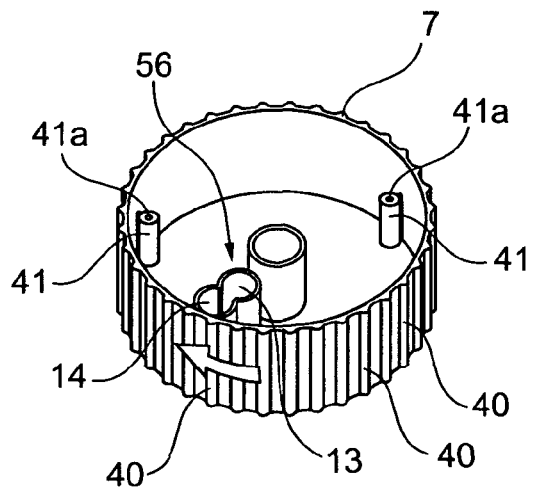
Figures 10A, 10B:
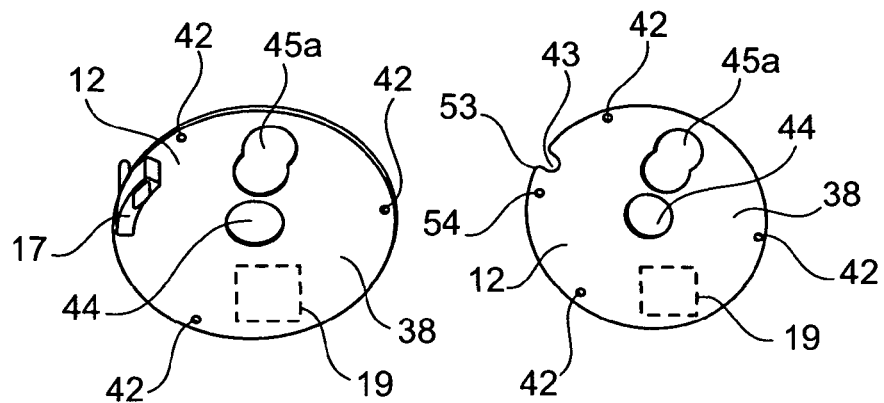
Figure 11:
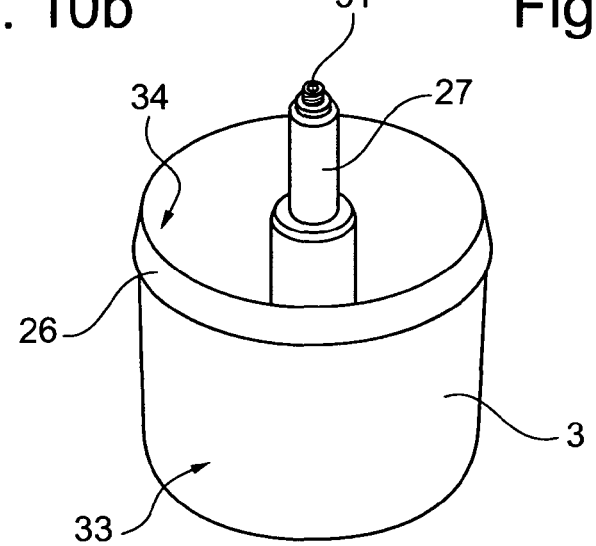
Figure 12:
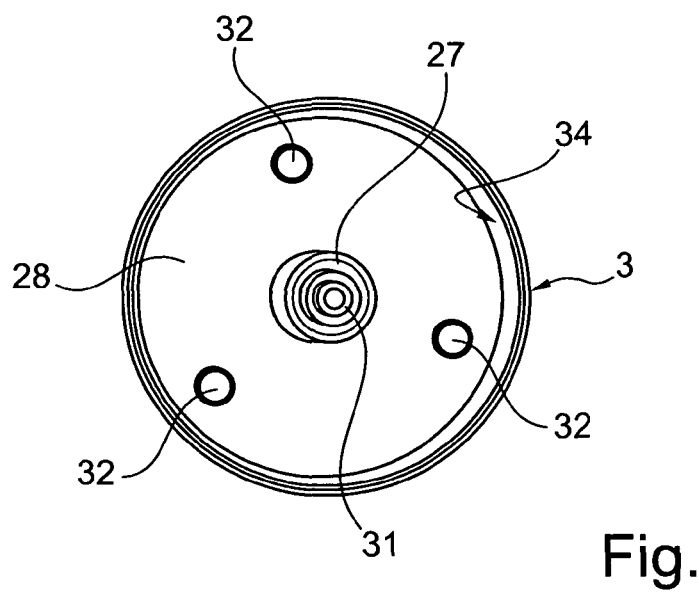
Figure 13:
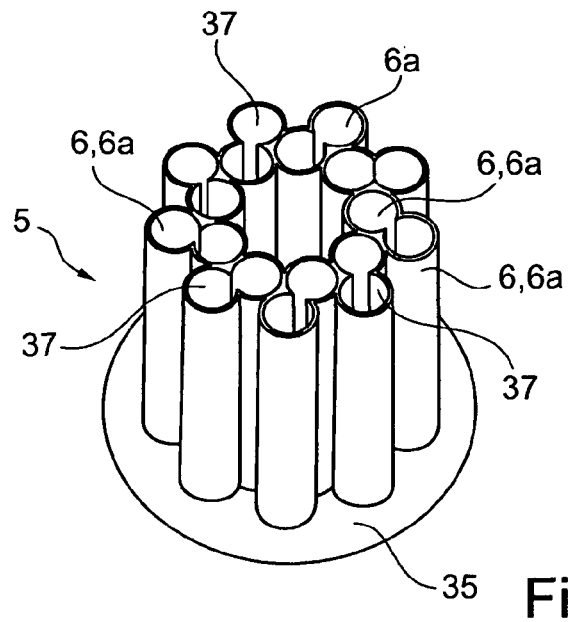
Figure 14:
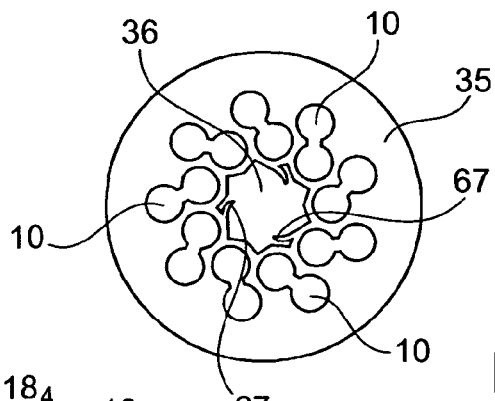
Figure 15:
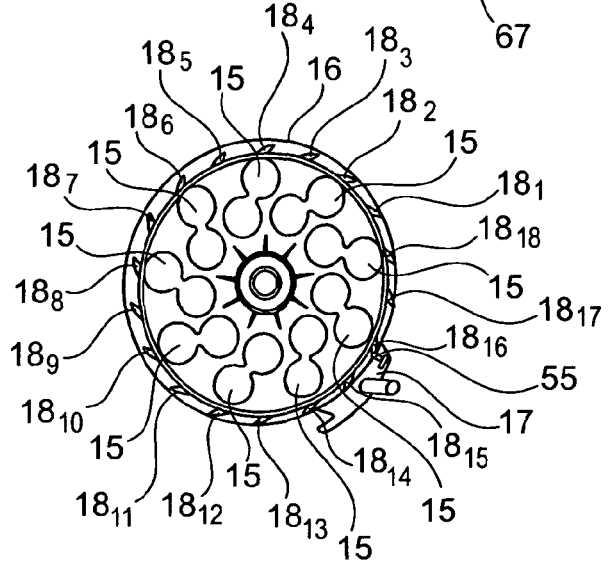
Figure 16:
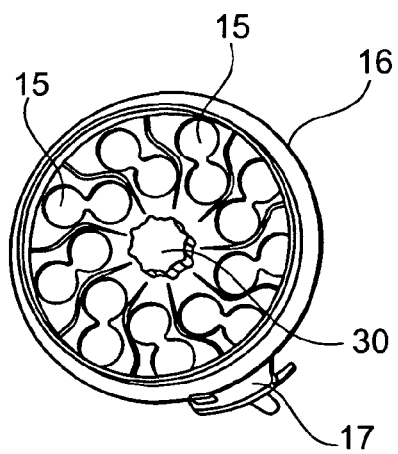
Figure 17:
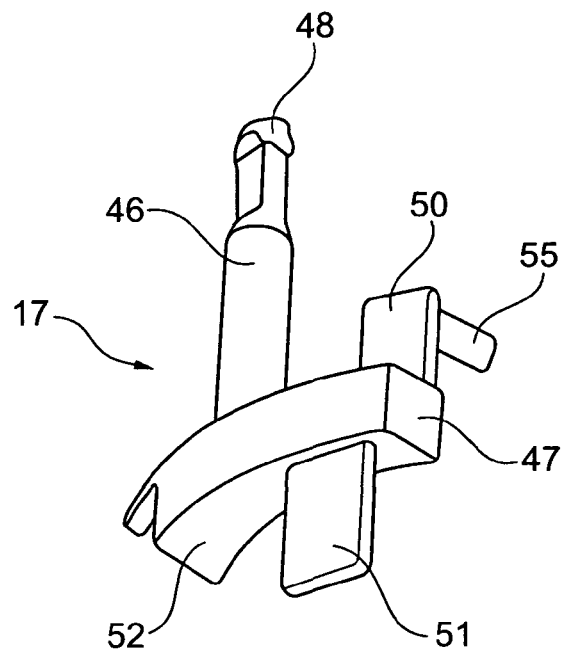
Figure 18:
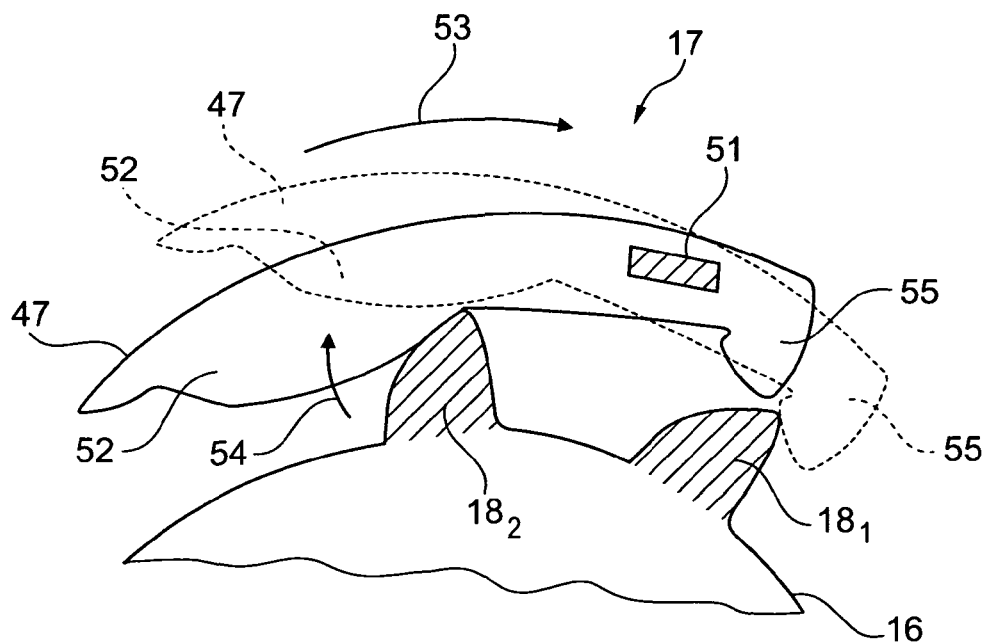
Figure 19:
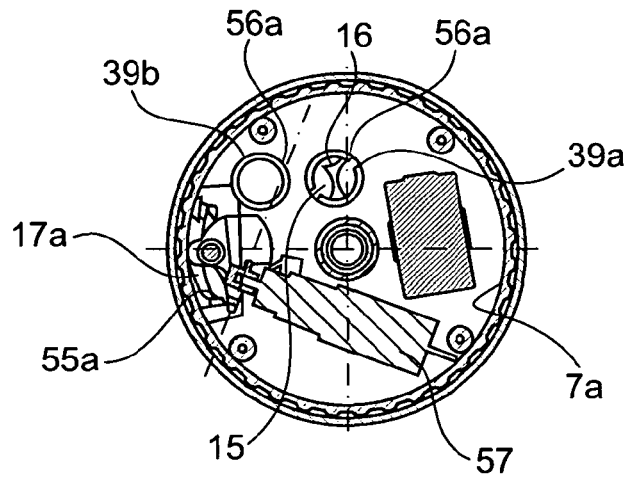
Figure 20:
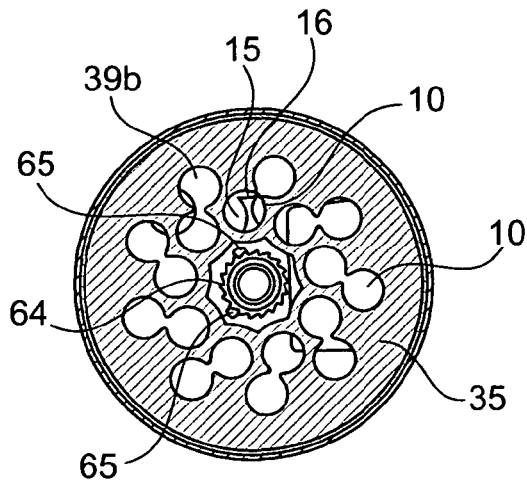
Figure 21:
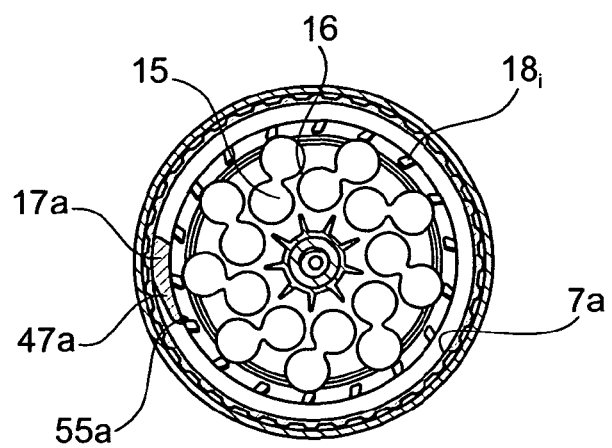
Figure 22:
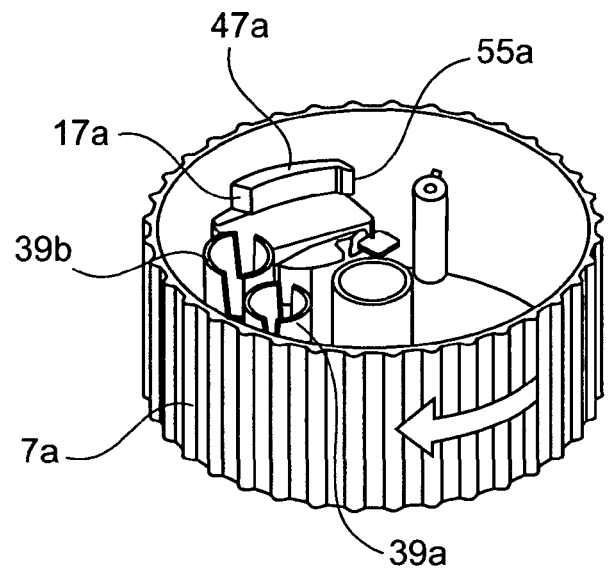
Figure 23:
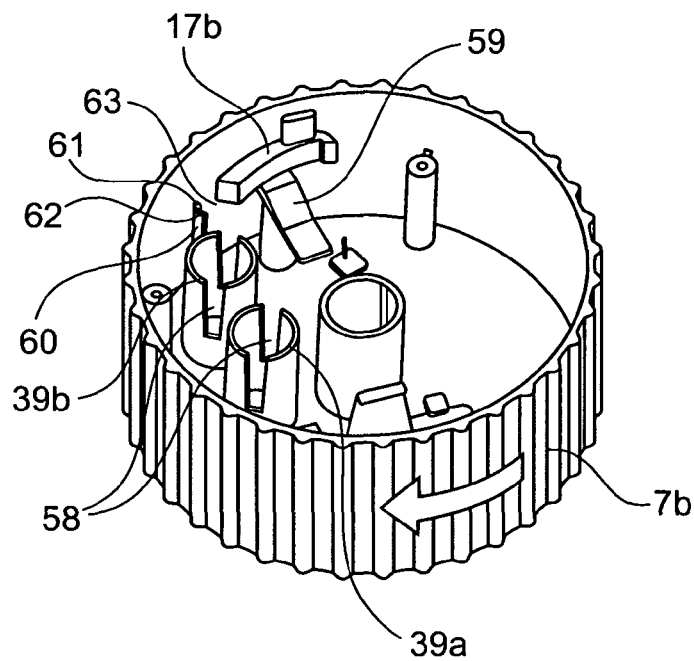
Figure 24:
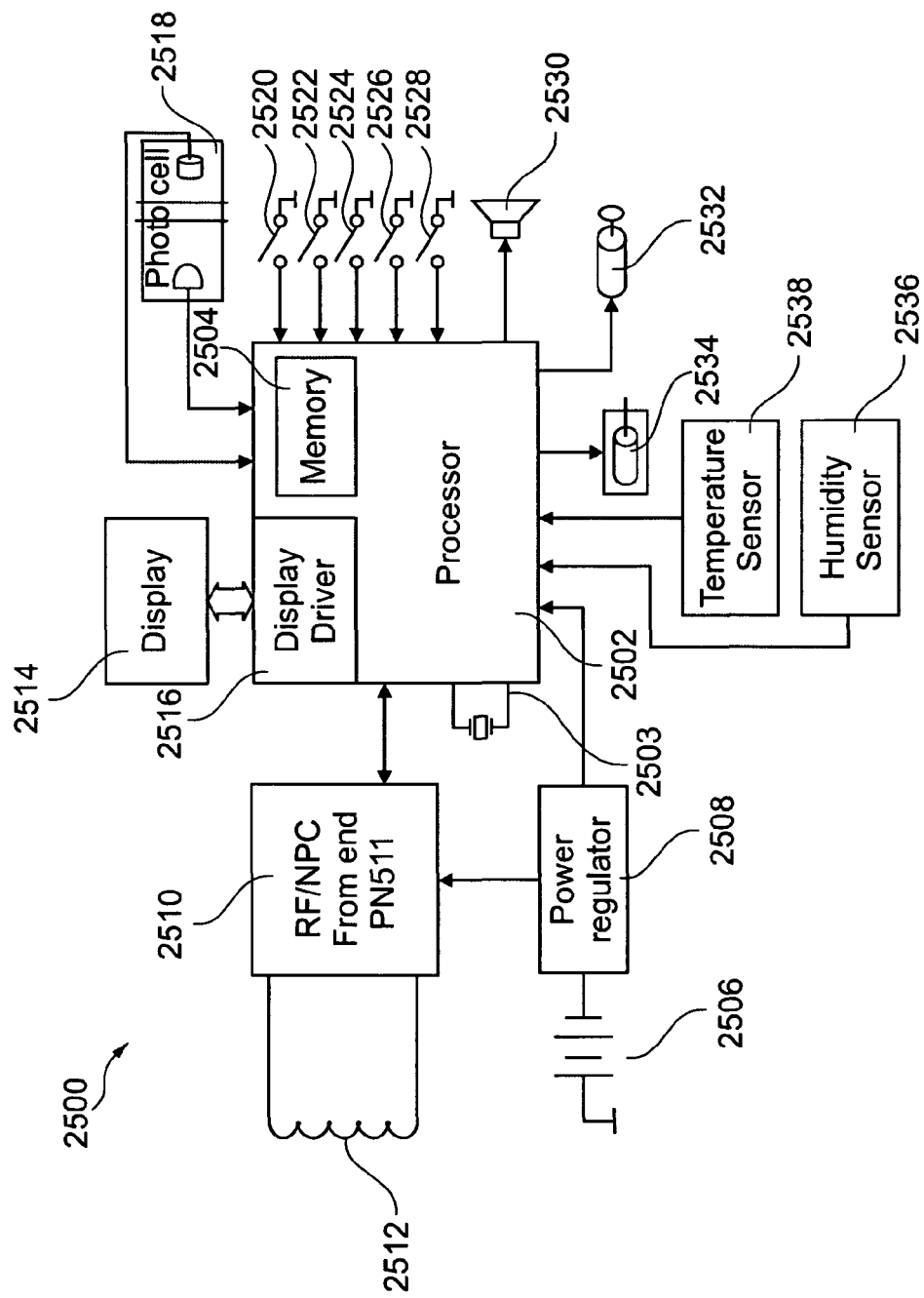
Figure 25:
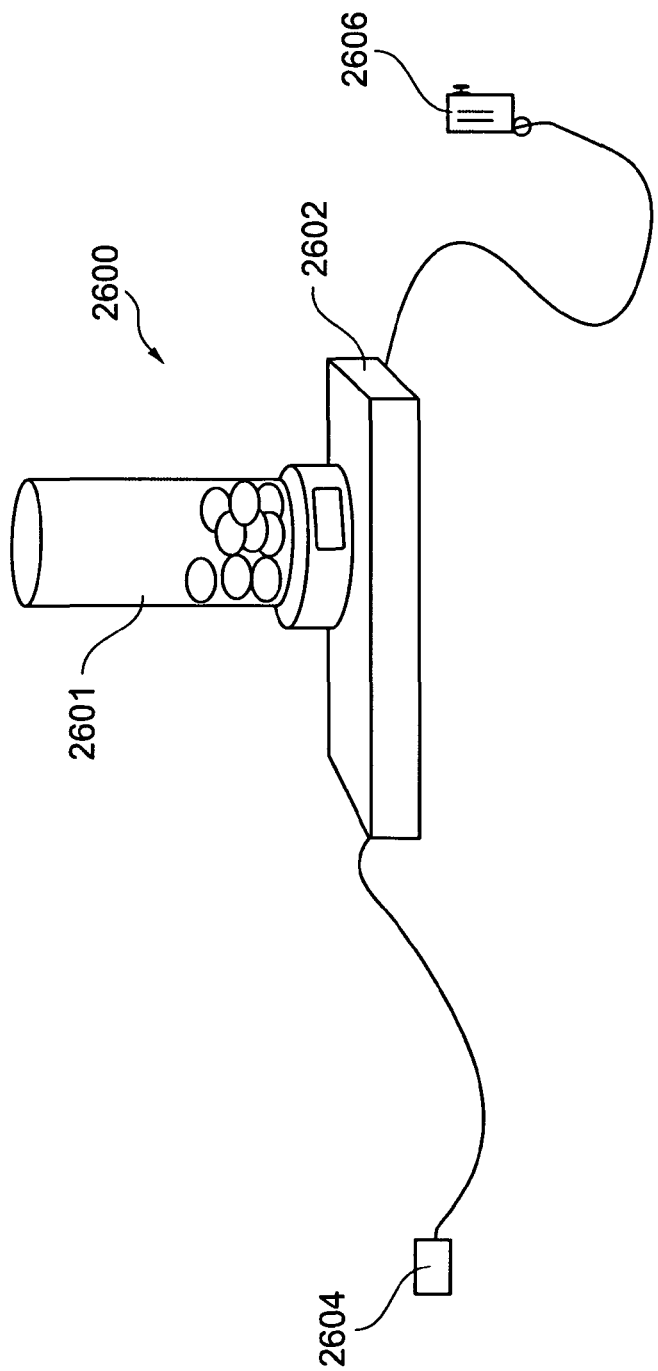
Figure 26:
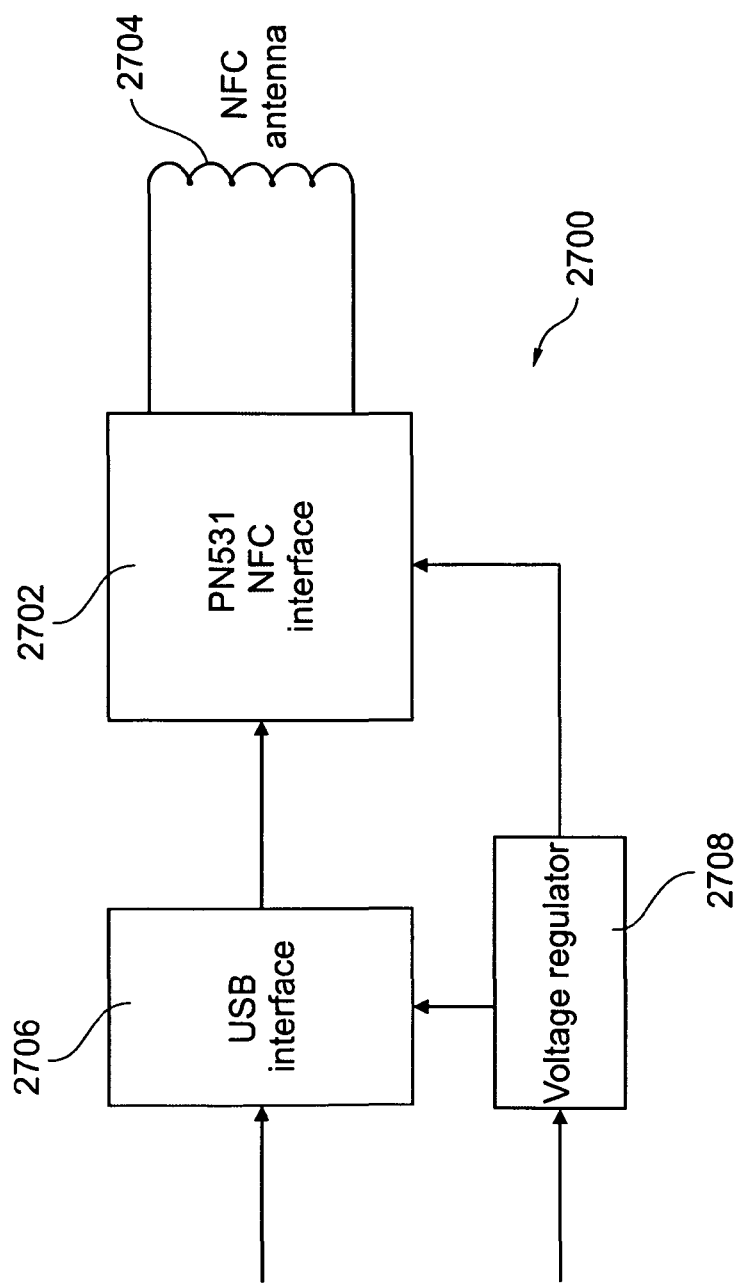
Figure 27:
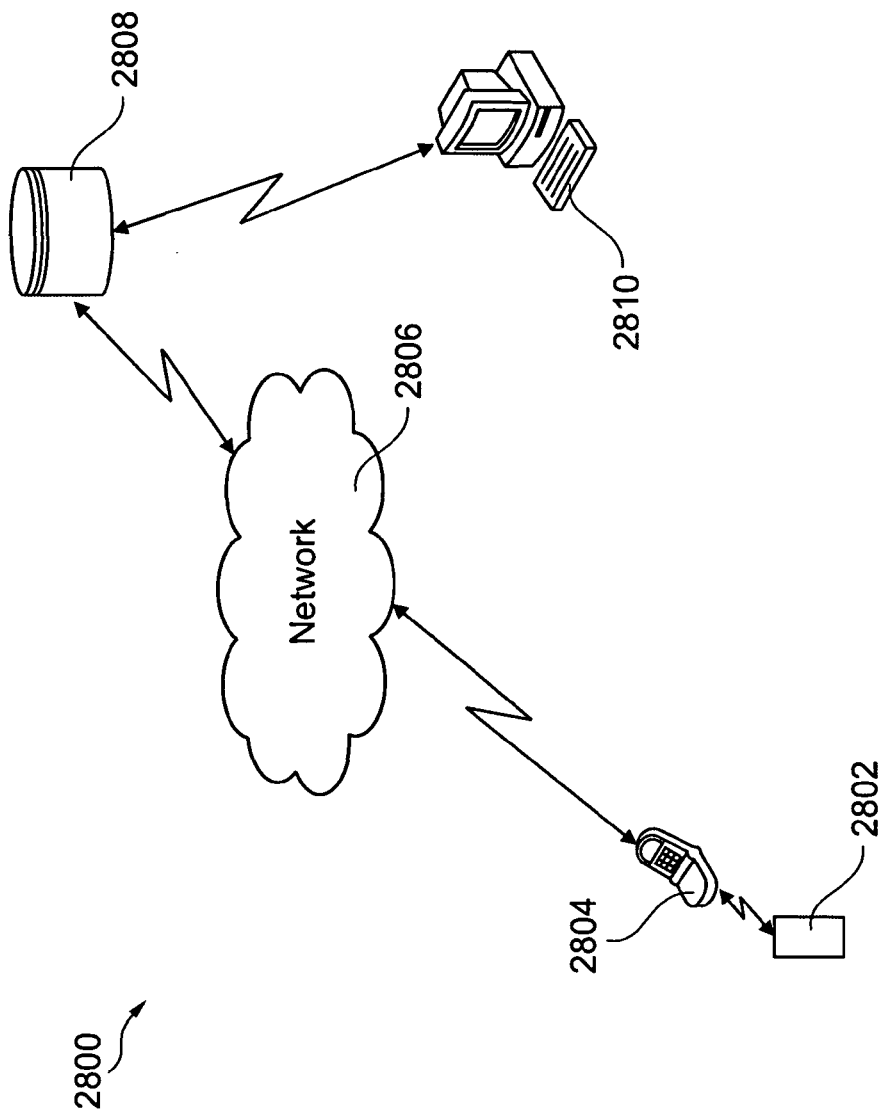
Figure 28:
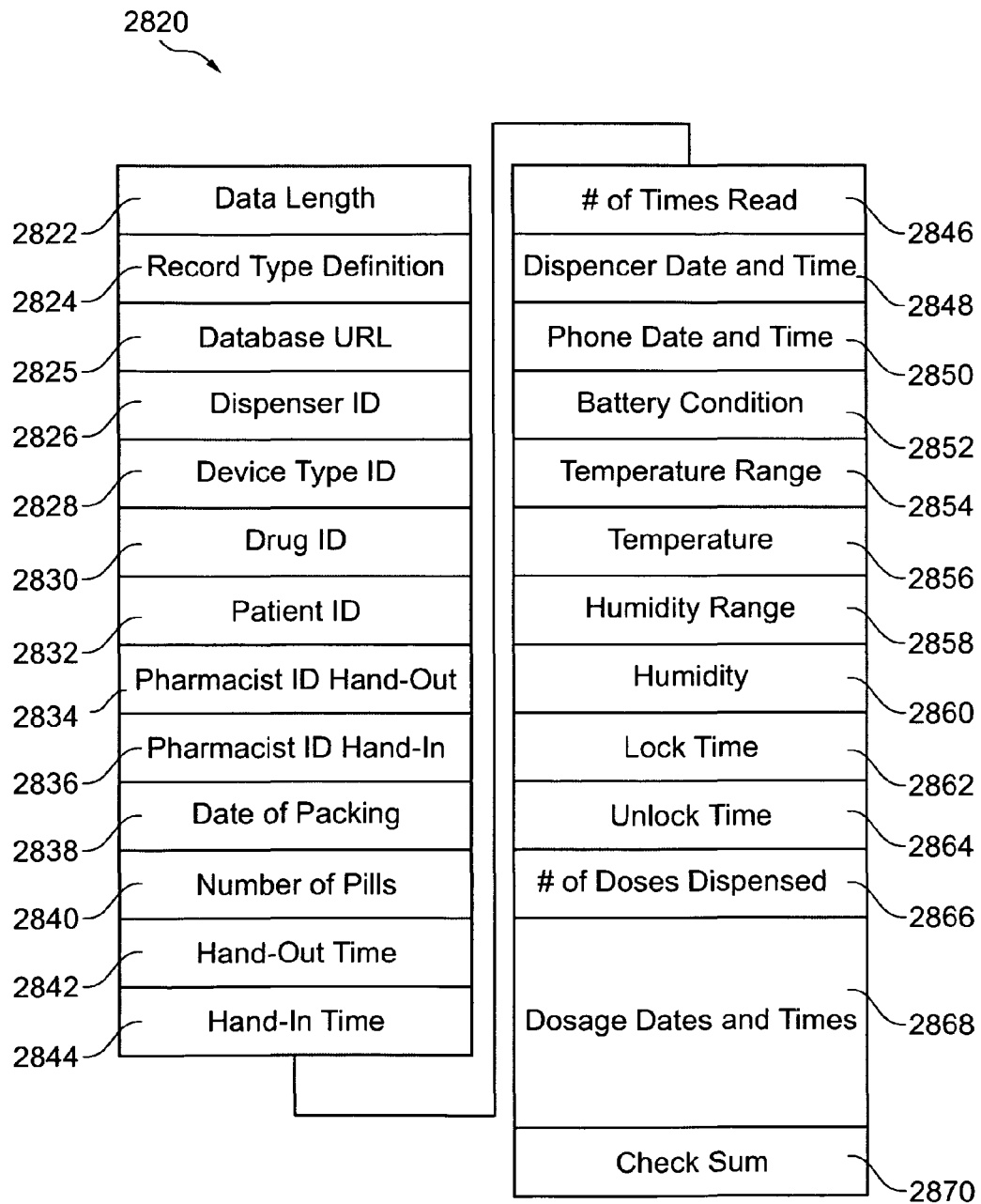
Figure 29A:
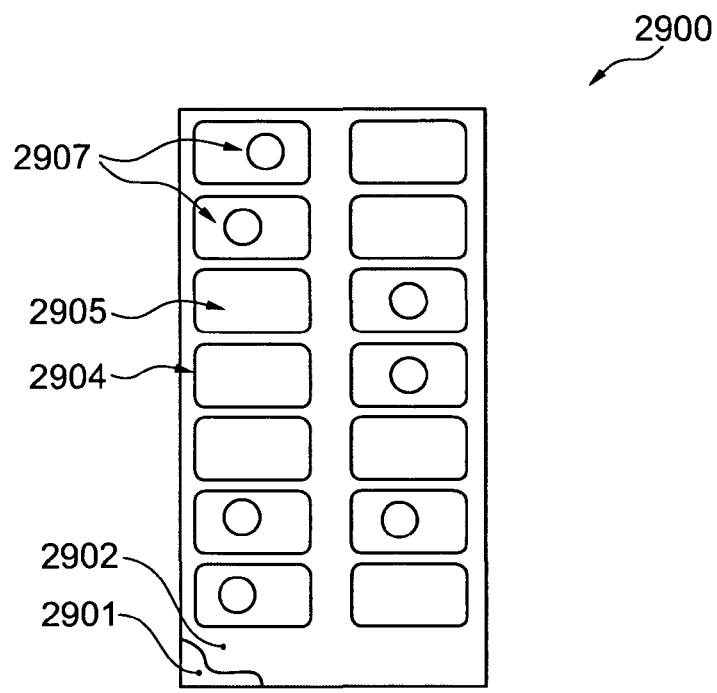
Figure 30A:
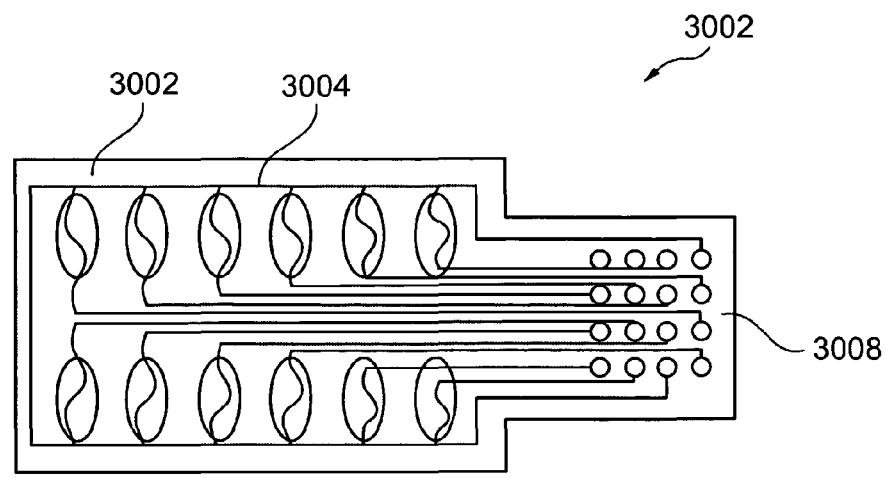

The invention will now be described in reference to the accompanying drawings of particular embodiments which are given by way of non limiting example. In the drawings shows:

FIG. 1 a size range of capsules to be dispensed,
FIG. 2 a side view of a dispenser,
FIG. 3 a schematic perspective view of the dispenser with the cover removed,
FIG. 4 a top view to the inner side of the cover,
FIG. 5 a schematic perspective view onto parts of the dispenser,
FIG. 6 a schematic perspective view onto parts of the dispenser,
FIG. 7 a schematic perspective view onto parts of the dispenser,
FIG. 8 a top view to the outer side of an indexing wheel,
FIG. 9 a perspective view to the inner side of the indexing wheel,
FIG. 10a, 10b a schematic perspective view onto an electronics disc, respectively,
FIG. 11 a perspective view onto a main housing,
FIG. 12 a top view to the inner side of the main housing,
FIG. 13 a schematic perspective view onto a reservoir,
FIG. 14 a top view onto a surface of a base of the reservoir,
FIG. 15 a perspective view onto the inner side of a capsule positioning disc,
FIG. 16 a perspective view onto the outer side of the capsule positioning disc,
FIG. 17 a perspective view onto an actuator,
FIG. 18 a diagrammatical view of the interaction between the actuator and stopper members,
FIG. 19 a cross sectional view onto a second embodiment of an indexing wheel,
FIG. 20 a cross sectional view onto a second embodiment of a base of a reservoir,
FIG. 21 a cross sectional view onto a second embodiment of an positioning disc,
FIG. 22 a perspective view onto a second embodiment of an indexing wheel,
FIG. 23 a perspective view onto a third embodiment of an indexing wheel,
FIG. 24 a diagrammatically view of a block diagram of the electronic circuit,
FIG. 25 a diagrammatically view of a system for communicating with a dispenser,
FIG. 26 a diagrammatically view of a block diagram of an electronic reader-writer device,
FIG. 27 a diagrammatically view of therapy compliance monitoring and communication means,
FIG. 28 a diagram showing the structure of a Near Field Communication data exchange format in accordance with an embodiment of the invention,
FIGS. 29A,B front and back views of a blister pack for use with a system in accordance with an embodiment of the invention, and
FIGS. 30A,B views of an alternative blister pack for use with a system in accordance with an embodiment of the invention.

The view in the figures is schematic and not fully scaled.

It shall be understood that the electronics disc described in the preceding and following examples for the dispenser according to present invention and shown as element of the dispenser in FIGS. 5 and 6 is an optional component of said dispenser. I.e., in one preferred embodiment of the invention, it is not a component of the dispenser. In another preferred embodiment of the invention, it is a component of the dispenser.

The invention as further described below refers to a dispenser 1 for dispensing a substance 2, especially in form of pharmaceutical or nutritional or confectionary capsules 2a or pills, in a unit dose manner. The dispenser 1 can be used for a range of capsule sizes. A list of commonly used capsule sizes for pharmaceutical products is shown by FIG. 1.

The dispenser 1 as shown by FIG. 2 is cylindrical in shape and consists of a housing 3 and a cover 4. The capsules 2a are stored within the dispenser 1 in a reservoir 5 (FIG. 3, FIG. 5) comprising a plurality of single compartments 6 which are arranged adjacent to one another in a circular arrangement, wherein adjacent sidewalls of the compartments are respectively connected to each other forming a circle. The present embodiment as now explained and described in more detail has eighteen capsule compartments 6, each in the form of a slim, vertical oriented cylindrical tube 6a to hold and contain capsules 2a stored therein. Each tube 6a can contain several capsules 2a arranged in an end-to-end orientation. In the present embodiment each tube 6a contains three capsules 2a.

For use the dispenser 1 is positioned with the cover 4 facing downward as shown in FIG. 3. To dispense a capsule 2a the cover 4 is removed from the housing 3 and an indexing wheel 7—and also the below explained indexing wheels 7a and 7b—is to be rotated in a clockwise manner, indicated by an arrow 8 on the indexing wheel 7. A mechanism permits the indexing wheel 7 to rotate a single index position until a receiving hole or receiving opening 9 (FIG. 8) of the indexing wheel 7 is positioned at an open end 10 (FIG. 5, FIG. 6) of one of the compartments 6 or cylindrical tubes 6a of the capsule reservoir 5, which is situated above the receiving opening 9 and a sliding surface 11 as shown by FIG. 8. At the same time the opposing dispensing opening 14 (FIG. 9) is positioned above an exit orifice 15 formed in a positioning disc 16. But, because the openings 9 and 14 are of a double-hole pattern 45 comprising two through holes 39a, 39b only one of the through holes will be connected to an open end 10 of a compartment 6, respectively, whereas the other one will simultaneously be connected to an exit orifice 15. As the receiving opening 9 and the dispensing opening 14 are connected by a connecting channel 13 these elements constitute a guiding member 56. The positioning disc 16 has the same pattern of exit orifices 15 as the reservoir 5 and/or the base 35 thereof has in respect to the pattern of open ends 10. But the positioning disc 16 and the reservoir 5 are dislocated in respect to each other for some degrees in the circumferential direction. Therefore, a capsule 2a delivered or dispensed from one open end 10 into the connecting channel 13 has to be transferred and moved to an exit orifice 15 by rotary/rotational movement of the guiding member 56 comprising the connecting channel 13. Therefore, at each time the free cross section of each of the open ends 10 is partly covered by a sectional material part of the positioning disc 16 in case that one of the holes 39a, 39b is aligned with an open end 19 or is covered by the sliding surface 11 of the indexing wheel 7. Due to this it is not possible for a capsule 2a to fall straight from an open end 10 through the receiving orifice 9, the dispensing opening 14 and an exit orifice 15 out of the dispenser 1. For dispensing a capsule 2a it is necessary to rotate the guiding member 56 in a clockwise direction by driving the indexing wheel 7 such, that a through hole 39a, 39b of the receiving opening 9 is moved from a position being aligned with an open end 10 to a position being aligned with an exit orifice 15, whereas simultaneously the respective other one of the through holes 39a, 39b is moved from its position being aligned with an exit orifice 15 to a position being aligned with one open end 10 of a compartment 6 of the reservoir 5. Due to this mechanism a capsule 2a falls first into the connecting channel 13 of the guiding member 56, but can not fall through due to the sectional material part of the positioning disc 16 covering or crossing the free cross section of the respective through hole 39a, 39b which is aligned with that compartment delivering a capsule 2a at this moment. Then the guiding member 56 being formed as the connecting channel 13 is turned one rotary/rotational step by driving the indexing wheel 7 until the respective through hole 39a, 39b which contains a capsule 2a is positioned above an exit orifice 15 so that the capsule 2a can fall out and leave the guiding member 56 by gravity. Simultaneously the respective other one of the through holes 39a, 39b has been moved during this same rotary/rotational step to a position to be aligned with one open end 10 of one compartment 6 now, so that it will receive a capsule 2a now. The connecting channel 13 is of such a height that it can contain only one of capsule 2a. Due to this mechanism it is possible to dispense one single dose unit during each rotary/rotational step of the guiding member 26 and the driving mechanism carrying out and controlling such a rotary/rotational stepwise motion or movement, even when a compartment 6 contains more than one capsule 2a.

The receiving opening 9 is formed in a substantially closed sliding surface 11 of the indexing wheel 7, which faces the open ends 10 of the reservoir 5, and extends through the indexing wheel 7 in form of the connecting channel 13 which terminates at an outside opening 14 of the indexing wheel 7. The outside opening 14 connects the connecting channel 13 to a hole or double-hole pattern 45a provided in an electronics disc 12. From this double-hole pattern 45a a capsule 2a falling down by gravity is guided to an exit orifice 15, which is formed in the (capsule) positioning disc 16, which is arranged at a short distance in front of the electronics disc 12. Thus, the connecting channel 13 is a part of a guiding means comprising the indexing wheel 7 and the electronics disc 12, which guiding means allow a capsule 2a to leave the dispenser 1 from an open end 10 of one compartment 6 to a dedicated exit orifice 15 of the positioning disc 16. The connecting channel 13 is rotatably arranged between the reservoir 5 and the positioning disc 16 and constitutes a guiding member 56 or at least a part of a guiding member which brings an open end 10 of a compartment 6 in dispensing communication with a respectively dedicated exit orifice 15 when a rotary or rotational step of the driving mechanism comprising the indexing wheel 7 is accomplished. The guiding member 56 itself is part of a driving mechanism which makes at least one of the components of the reservoir 5 and the positioning disc 16 and the guiding member 56, 56a to rotate and comprises an actuator 17, 17a, 17b. In one embodiment the driving mechanism comprises an indexing wheel 17, 17a, 17b which comprises the respective guiding member 56, 56a. A capsule 2a contained in the cylindrical tube 6a is guided to the dedicated exit orifice 15 and falls out of the dispenser 1 by gravity when all respective holes and/or openings 9, 14, 15 are situated one above the other.

An electronic sensor in the dispenser apparatus 1 detects the capsule 2a leaving the dispenser apparatus 1 and records the information onto a memory chip 19 arranged on the electronics disc 12. The dispenser 1 cannot be indexed again until the cover 4 is replaced onto the housing 3 of the dispenser 1. When the cover 4 is seated onto the housing 3 again, an internal stop or lock provided by an actuator 17 which releasably engages one of a plurality of stopper members $18_1$, $18_2$, $18_3$, ..., $18_{17}$, $18_{18}$ formed on the rim portion of the inner side of the positioning disc 16 is released by a releasing member 24 provided at the cover 4 enabling the dispenser 1 to be indexed again by rotating the indexing wheel 7 the next time the cover 4 is removed. Dispense information stored on the memory chip 19 can be transferred to an external device using bluetooth or RFID or other wireless communication. A RFID antenna may be incorporated in the electronics disc 12.

In the above described embodiment a number of 18 stopper members is exemplarily described. However, it shall explicitly be noted that in the whole context of the invention, including the embodiments described hereinafter, the amount of stopper members does not affect the fundamental mechanical interaction between the actuator and the stopper members. In other words the amount of stopper members may be chosen in accordance with the number of desired rotational steps.

The dispenser apparatus 1 may be constructed from a range of packaging materials, most preferable are thermoplastic resins. The cover 4 and main housing 3 can be made of HDPE (High Density Polyethylene) or PP (Polypropylene). The material should provide enough structural integrity to withstand up to 100 capsule indexing cycles. In addition, the materials should enable the dispenser 1 to be dropped from a distance of 1 meter without sustaining significant damage that would prevent normal dispensing operation. Finally, the materials should protect the capsules 2a from moisture. The materials should have a low moisture vapour transmission rate.

The cover 4 forms a moisture tight seal with the main housing 3. The cover 4 may contain a desiccant to maintain a low relative humidity environment within the capsule dispenser. Preferably the cover 4 may consist of two materials: a HDPE (High Density Polyethylene) or PP (Polypropylene) outer surface 20 and an inner surface 21 composed of a desiccant plastic. The two-material cover 4 may be overmoulded, in a two-shot injection-moulded process.

The cover 4 is cylindrical in shape, consisting of a base 22 and a circumferential sidewall 23. The base 22 has a releasing member 24 in the form of a ridge 24a or a raised profile that extends radially along the inside surface 21 of the sidewall 23. When the cover 4 is seated on the dispenser 1 the ridge 24a or the raised profile presses down on a component of the actuator 17 to unlock the indexing mechanism. The cover 4 has a sealing surface 25, located at the open end of the cover 4 along the inside surface 21 of the sidewall 23. This sealing surface 25 in the cover 4 engages the housing 3 at its circumferential engaging surface 26 when the cover 4 is seated onto the dispenser 1.

The housing 3 (FIG. 11, FIG. 12) is cylindrical in shape with a shaft 27 that extends from the base 28. A capsule dispenser sub-system 29 comprising the reservoir 5, the indexing wheel 7, the electronics disc 12, the (capsule) positioning disc 16 and the actuator 17 is assembled into the housing 3. The capsule dispenser sub-system 29 is secured into main housing 3 using a thread-cap or threaded nut 30 that screws onto the end 31 of the main housing shaft 27. The reservoir 5 and the positioning disc 16 are fixed whereas the indexing wheel 7 is rotatably arranged at the shaft 27. Within the housing 3 there are circular profiles 32 provided on the base 28 and orientated equally about the inside surface of the housing base 28. The (capsule) reservoir 5 has features that engage with the circular profiles 32 in the housing 3 to prevent the reservoir 5 from rotating when the dispenser 1 is in use.

The housing 3 forms a moisture tight seal with the cover 4. The housing 3 may contain a desiccant to maintain a low relative humidity environment within the capsule dispenser apparatus 1. The main housing 3 preferably consists of two materials: a HDPE (High Density Polyethylene) or PP (Polypropylene) outer surface 33 and an inner surface 34 composed of a desiccant plastic. The two-material housing 3 may be overmoulded in a two-shot injection-moulded process.

The capsule dispenser sub-system 29 resides within the housing 3 and comprises the guiding means composed by the guiding member 56 building the connecting channel 13 of the rotatable arranged indexing wheel 7 providing the substantially closed sliding surface 11 and the double-hole pattern 45 of the electronics disc 12. It also comprises a driving means or driving mechanism which comprises the indexing wheel 7 and the actuator 17.

The reservoir 5 contains a series of compartments 6 in the form of the cylindrical tubes 6a that hold the capsules 2a in an end-to-end manner. The reservoir 5 is composed of eighteen tubes 6a or compartments 6, arranged in an inner and outer circular set of nine tubes respectively. Each compartment 6 or tube 6a may hold one to ten capsule(s) 2a. The number of capsules 2a in each compartment 6 or tube 6a dependents on the size of the capsules 2a and/or the overall size of the dispenser 1 or the cylindrical tubes 6a. The reservoir 5 has a circular base 35 on which the compartments 6 or cylindrical tubes 6a extend outward. Each of the cylindrical tubes 6a has an open end 10 provided in the base 35 and has an opposing open end 37 at its opposite side. The shaft 27 of the housing 3 extends through the centre 36 of the capsule reservoir base 35.

In this embodiment the reservoir 5 is dimensioned to hold three capsules 2a in an end-to-end position. The capsules 2a are indexed one-by-one out of the dispenser 1 using gravity. In this embodiment, the capsule reservoir 5 is made in an injection moulding process, wherein the (capsule) reservoir 5 is preferably made of HDPE (High Density Polyethylene) or PP (Polypropylene). It is also possible to make the reservoir 5 of desiccant plastic.

The indexing wheel 7 is positioned on top of the (capsule) reservoir base 35 with its sliding surface 11 closing most of the open ends 10 of the cylindrical tubes 6a. The indexing wheel 7 is fixed into position by the shaft 27 of the housing 3. The indexing wheel 7 has a set of two through holes 39a, 39b that are joined together, forming two intersecting circular shapes that intersect and that constitute the receiving opening 9 at one side and the dispensing opening 14 at the opposite side. In this embodiment, the intersecting-hole configuration enables a single sensor to detect a capsule 2a dispensed from either the inner 39a or outer through hole 39b. It is also possible that in another embodiment, the circular shaped holes 39a, 39b do not intersect.

The double hole-arrangement in the indexing wheel 7 is used in conjunction with the positioning disc 16 to guarantee that only one capsule 2a is dispensed during an index cycle. One of the through holes 39a, 39b is aligned with a specific capsule reservoir tube 6a as the indexing wheel 7 rotates about the circular reservoir base 35. The through holes 39a, 39b are arranged in such a manner that the inner through hole 39a is able to be brought into dispensing communication with the open ends 10 arranged in the inner circle of base 35 and the exit orifices 15 of the inner circle of the positioning disc 16. Likewise the outer through hole 39b will be able to communicate with the open ends 10 and the outer exit orifices 15. In an alternating manner a substance 2 or a capsule 2a will be dispensed from an inner and an outer exit orifice 15 respectively.

The indexing wheel 7 has a series of ribbed features 40 along the outside surface. These ribs 40 are used as a gripping surface when the indexing wheel 7 is rotated during a capsule index cycle.

The indexing wheel 7 houses the dispenser electronics and the other capsule indexing components. The electronics disc 12 is assembled onto a set of three posts 41 in the indexing wheel 7. These posts 41 have threaded holes 41a so that the electronics disc 12 can be secured on to the indexing wheel 7 using screws that extend through assembling holes 42 provided in the electronics disc 12.

FIGS. 5 and 6 shows a view of the capsule dispenser sub-system 29 with the indexing wheel 7 removed. The following components are visible: reservoir 5, actuator 17, threaded nut 30 or cap, electronics disc 12 and positioning disc 16.

The electronics disc 12 is assembled on to the indexing wheel 7 and houses the electronic components for the capsule dispenser 1. The electronics disc 12 is fixed to the indexing wheel 7 by placing threaded fasteners through the three assembling holes 42 and the corresponding threaded holes 41a along the disk perimeter. The actuator 17 is fitted through a cut out 43 along the perimeter of the electronics disc 12. The electronics disc 12 has a through hole 44 to be assembled onto the main housing shaft 27 and has the double-hole pattern 45a so that a capsule 2a can pass through. The surface 38 of the electronics disc 12 faces the inner side of the capsule disc 16 at a short distance.

When the electronics disc 12 is assembled onto the indexing wheel 7 a compartment is created within the indexing wheel 7 for containing the electronic components. The electronic components include: a power supply (i.e., battery), an inlay that contains the memory chip 19 and antenna and capsule detection sensor(s). The electronic disc 12 may include a motor or solenoid that is used to control the actuator 17 remotely as an alternative to actuator control by seating the dispenser cover 4 (i.e., not by seating the dispenser cover). Such an embodiment is explained later on below in respect to FIG. 19 to 22.

The actuator 17 as shown in FIG. 17 enables the dispenser 1 to index one position. The actuator 17 consists of a vertical shaft 46 or post and a horizontal member 47. One end 48 of the vertical shaft 46 or post is fitted into a hole 49 of the indexing wheel 7; the other end of the vertical shaft 46 is attached to the horizontal member 47 of the actuator 17. The vertical shaft 46 extends through the cut-out 43 of the electronics disc 12.

The horizontal member 47 of the actuator 17 has two posts: a sensor mounting post 50 and an actuator tab 51. The sensor mounting post 50 extends along the same side as the vertical shaft 46. One or more sensors can be mounted on the sensor mounting post 50. The at least one sensor monitors a capsule 2a on its way between the double-pattern 45 and the exit orifice 15 when the capsule 2a leaves the dispenser apparatus 1 through an exit orifice 15. To allow direct access to a capsule 2a for monitoring the connecting channel 13 may be provided with one or more slits 58 (FIG. 23). In the present embodiment one sensor is used to monitor capsules 2a leaving the dispenser 1 from both the inner and outer hole positions according to the inner and outer set of tubes 6a. But it is also possible that two sensors are used: one for the inner hole position and one for the outer hole position.

On the distal end of the horizontal member 47 is a stopper notch 55 or tooth that engages with tooth like stopper members $18_1$, $18_2$, $18_3$, $18_1$, $18_5$, $18_6$, $18_7$, $18_8$, $18_9$, $18_{10}$, $18_{11}$, $18_{12}$, $18_{13}$, $18_{14}$, $18_{15}$, $18_{16}$, $18_{17}$ and $18_{18}$ formed on the positioning disc 16. After the capsule dispenser 1 is indexed one position, the stopper notch 55 on the horizontal member 47 of the actuator 17 captures one tooth like stopper member $18_1$ to $18_{18}$ in the capsule positioning disc 16, preventing the dispenser 1 from indexing again. The dispenser 1 is locked.

To unlock the (capsule) dispenser 1 and the indexing wheel 7 again, the actuator tab 51 engages with the ridge 24a in the cover 4 when the cover 4 is fully seated onto the dispenser housing 3. When the ridge 24a in the cover 4 contacts the actuator tab 51, the actuator 17 rotates about vertical shaft 48 and the stopper notch 55 comes out of its blocking contact with one of the stopper members $18_1$ to $18_{18}$. The stopper notch 55 comes free from this respective tooth like stopper member $18_1$ to $18_{18}$ and the dispenser 1 is now unlocked.

In the following a movement of the actuator which is caused during a rotary/rotational step is described amongst other things. This movement may be seen as automatically initiated by accomplishing a rotary step.

In this unlocked position the horizontal bar 47, 47a is in a position as shown by FIG. 18 in continuous line. The stopper notch 55 has abandoned its stoppage and blocking position and has moved away from its blocking contact with stopper member $18_1$. Now the indexing wheel 7 and the actuator 17 are turned in the direction of the arrow 53 for starting the next rotary/rotational step of the guiding member 56. Having started this next step a guiding notch 52 radially inwardly extending from the horizontal bar or member 47 comes into contact with the stopper member $18_2$ arranged adjacent to the stopper member $18_1$ in the direction contrary to the rotary direction as indicated by the arrow 53. The guiding notch 52 now interacts with the stopper member $18_2$ in such a manner that the horizontal member 47 during further rotary movement of the indexing wheel 7 is pivoted outwardly as indicated by the arrow 54 into a position as shown by dotted lines in FIG. 18. Due to this move the stopper notch 55 again immerges into a space between the stopper member $18_1$ and the next stopper member ($18_2$, not shown) which follows in the directional direction (arrow 53). The rotary/rotational step is finished, when the stopper notch 55 comes into blocking contact with the next following stopper member ($18_{18}$) again, which stopper member constitutes a stoppage. During such a rotary/rotational step the through holes 39a, 39b are moved from a position being aligned to an open end 10 to a position being aligned with an exit orifice 15 or from a position being aligned to an exit orifice 15 to a position being aligned to an open end 10, respectively and vice versa during the next following rotary/rotational step. Thus, the actuator 17 (and also the actuator 17a) comprises a stopper notch 55 (55a of actuator 17a) and a guiding notch 52, wherein the guiding notch 52 interacts with one of the stopper members $18_1$, $18_2$, $18_3$, ..., $18_{17}$, $18_{18}$ for carrying out a radially inwardly directed rotational movement of the respective stopper notch 55 (55a) during each rotary/rotational step of the one rotatably arranged component of the reservoir 5 and the positioning disc 16 and the guiding member 56 (56a of actuator 17a) and the respective indexing wheel 7, 7a to bring the respective stopper notch 55, 55a into a blocking contact with another one, preferably an adjacently arranged one, of the stopper members $18_1$, $18_2$, $18_3$, $18_1$, $18_5$, $18_6$, $18_7$, $18_8$, $18_9$, $18_{10}$, $18_{11}$, $18_{12}$, $18_{13}$, $18_{14}$, $18_{15}$, $18_{16}$, $18_{17}$ and $18_{18}$ afterwards for accomplishing the rotary/rotational step.

In another embodiment, the actuator rotation may be accomplished by using a motor 57 or solenoid mounted in the capsule dispenser 1. The motor or solenoid may be controlled using an onboard computer within the capsule dispenser 1 or from an external device. In such an embodiment it is possible that the external device sends a signal to the dispenser apparatus by RFID communication or that bluetooth communication or any other wireless communication is used.

The positioning disc 16 is shown in FIGS. 15 and 16 with the actuator 17 and the threaded nut 30 assembled. The positioning disc 16 is in the form of a circular-shaped component with a series of holes of which each constitutes an exit orifice 15: one for each compartment 6 or cylindrical tube 6a of the reservoir 5, i.e. each one may be brought into dispensing communication with one dedicated open end 10. These holes correspond to the positions of the compartments 6 or cylindrical tubes 6a in the capsule reservoir 5, but a little bit dislocated or staggered for some degrees in the circumferential direction. On the inner surface of the positioning disc 16, a series of eighteen tooth like stopper members $18_1$ to $18_{18}$ are positioned radially around the perimeter at a rim portion of the positioning disc 16. Each of the stopper members $18_i$, (with i=1 to 18) enables a through hole 39a, 39b in the indexing wheel 7 to be positioned at one discrete compartment 6 or cylindrical tube 6a of the inner or outer circular arrangement. The positioning disc 16 has a hole in its centre for assembly onto the main housing shaft 27.

When the indexing wheel 7 is rotated, the actuator 17 permits the positioning disc 16 to rotate position, until the notch 52 of the actuator 17 engages the next toothlike stopper member $18_i$ in the positioning disc 16.

As shown by FIGS. 19 and 22 it is also possible to incorporate into the housing 3 a motor 57 or a solenoid within an indexing wheel 7a which locks the actuator 17a in its stoppage position when the stopper notch 55a is in engaging contact with one of the stopper members $18_1$ to $18_{18}$. Furthermore the motor 57 or solenoid pushes the actuator 17a back into its unlocked position with the notch 55a being released from the stopper members $18_1$ to $18_{18}$. For these purposes the actuator 17a is provided with a motor driven spindle which locks the actuator 17a in its stoppage position when it is in engagement with one stopper member $18_1$ to $18_{18}$ and which pushes the actuator 17a back to its unlocked position. Thus, the actuator 17a makes the same pivotal movement as the actuator 17, but it is not necessary to have an actuator tab 51 provided on the horizontal member 47a any longer. This can be realized by a spirally formed wheel connected to the spindle which fetches an arm of the actuator 17a so that the actuator 17a can not be pivoted outwardly and the indexing wheel 7a can not be rotated by a user. By an external signal (e.g. the user holds his NFC phone against the dispenser and sends a signal to the motor 57), the motor turns the spirally formed wheel into a position releasing the fetched arm of the actuator 17a and further pivots the actuator 17b in its open position ready to rotate. The user than rotates the indexing wheel 7a until it reaches its next stoppage or blocked position. The actuator 17a drives two switches, one to awake the electronics that then read and detect the capsule dispensing, and the other to stop the motor 57 again.

It is also possible that a motor and/or the solenoid and/or the spindle drive the indexing wheel 7, 7a, 7b. In such a case it would not be necessary to have an actuator 17, 17a, 17b anymore which operates the locking and unlocking motion/movement because this function could then completely be transferred to and carried out by the motor and/or solenoid and/or spindle driven mechanism which directly drives the indexing wheel 7, 7a, 7b. Such a mechanism may be driven by electrically or hydraulically provided power.

Furthermore it is possible to have commands and/or signals provided from an external source for controlling the driving mechanism which makes the indexing wheel 7a to rotate stepwise and/or which makes the actuator 17a to move into its locked position and/or back to its unlocked position. Such a driving mechanism can comprise an electric or hydraulic motor which is controlled by such external commands and/or signals.

The dispenser 1 further may comprise means for monitoring and controlling administration of medications and for communication which comprise electronics which are situated on or within the electronics disc 12 and/or within the compartment formed within the indexing wheels 7, 7a between the electronics disc 12 and the inner surface of the respective indexing wheel 7, 7a opposing the sliding surface 11.

From FIG. 20 it can be taken, that although an open end 10 is aligned with the (not visible) through hole 39a the dispensing of a capsule 2a is not possible due to a material section of the positioning disc 16 being positioned beneath. Also it can be seen that the other through hole 39b is not in a receiving communication with any one of the open ends 10. The respective position of the through holes 39a and 39b can also be seen from FIG. 19 which shows the position of the indexing wheel 7a at the same time.

FIG. 21 shows the corresponding position of the positioning disc 16 at this same moment.

FIG. 23 represents another embodiment of an indexing wheel 7b for mechanical version (without an electro motor 57) with separated, not intersecting through holes 39a, 39b, each being provided with two diametrically opposing slits 58 which allow a sensor to detect the dispensing of a capsule falling through a hole 39a, 39b. Furthermore the actuator 17b of the indexing wheel 7b is provided with an arm 59 which arm by starting the rotating of the indexing wheel 7b again switches the electronics on.

Furthermore FIG. 23 shows a bar like post 60 which is provided with two holes 61, 62. Additionally the actuator 17b is provided with nose 63 having a downwardly extending little pin which matches with the hole 61 in the locking or stoppage position of the actuator 17b and which matches with the hole 62 in the non-locked position of the actuator 17b ready for rotating together with the indexing wheel 7b. The little pin clicks in either of these two holes 61, 62 so that the actuator is precisely locked in its closed/locked position or its open position ready for rotating. Due to this feature the actuator will not move in case that the dispenser is subject to vibration or shock until the indexing wheel 7b is driven.

In all the above mentioned figures identical elements, members or parts having the same reference number are identical ones or at least of the same function although when used at different embodiments of the invention.

FIG. 20 shows a toothed wheel 64 which is in contact with ribs 65 so that it is hindered to rotate in a contraclockwise direction. Due to this the indexing wheel 7a can only carry out a clockwise rotation. For the same purpose the base 35 of the embodiment according to FIG. 14 comprises latching arms 67 for interacting with a not shown toothed wheel.

FIG. 24 shows a block diagram of the electronic circuit 2500 for use in monitoring and controlling administration of medications and for communication. The electronic circuit 2500 includes a processor 2502, which may, for example, be an 8-bit microcontroller, such as a P89LPC936, developed by Philips and available from NXP Semiconductors Netherlands B.V. Of course, it will be understood that other processors or microcontrollers may also be used in the electronic circuit 2500. In some embodiments, the processor 2502 may be clocked by an external clock or crystal 2503.

The processor 2502 may include a memory 2504, for storing programmed instructions for the processor 2502 and/or data used by the electronic circuit 2500. Alternatively, the memory 2504 may include one or more external memory devices (not shown). The memory 2504 may include non-volatile memory, such as flash memory, EEPROM memory, or static memory, and/or volatile memory, such as DRAM.

The electronic circuit 2500 is powered by a battery 2506, which may have its electrical characteristics adapted to the needs of the electronic circuit 2500 by a power regulator 2508. The battery 2506 may be a conventional replaceable battery, or a rechargeable battery, which may be recharged, for example, when the device is connected to a docking station (see below). The power regulator 2508 may also include the ability to detect the status of the battery 2506, and provide the status information to the processor 2502. In some embodiments, an additional battery measuring device (not shown) may be used to measure the status of the battery 2506. The processor 2502 communicates with a first transceiver 2510, which communicates wirelessly with other electronic devices via a first antenna 2512. The first transceiver 2510 uses radio frequency (RF)-based communication, such as Near Field Communication (NFC) or other wireless communication technologies suitable for short-range and/or low-power wireless communication, such as other RFID technologies, Bluetooth, or ZigBee. Where power considerations permit longer range communications, other wireless communications technologies, such as Wi-Fi, WiMAX, or various cellular technologies may be employed.

In some embodiments, where the device includes an optional display 2514, the processor 2502 may further include a display driver 2516, to operate the display 2514. In some embodiments, the display driver 2516 may be implemented at least in part as driver software. In some embodiments, the display driver 2516 may be a separate device (not shown), rather than being included in the processor 2502.

As discussed above, in dispenser embodiments, an optical detector 2518, such as a laser detector, an LED and detector, an infrared LED and detector, or other opto-electronic detection device, may be used to determine when a solid preparation, such as a pill, has been dispensed by the device. A signal from the optical detector 2518 is provided to the processor 2502 for evaluation. In some embodiments, where there are multiple optical detectors (not shown), such as where there are multiple dispensing paths for pills, in which case one such detector may be present in each such path, signals from each of these the optical detectors are provided to the processor 2502.

The electronic circuit 2500 may also include numerous control switches for adjusting the settings of the processor 2502 and/or of the electronic circuit 2500. For example, a first switch 2520 can be used to activate or deactivate the electronic monitoring and communication. A second switch 2522 can be used to detect opening of the container, such as by removing or opening the container lid, or removing the dispenser from the container. In some dispenser embodiments, this may indicate tampering with the dispenser. Third and fourth switches 2524 and 2526 may be used, for example, for setting the time in hours (third switch 2524) and minutes (fourth switch 2526). A fifth switch 2528 may be used to select use of an audible alarm, such as a buzzer 2530, which may be sounded when, for example, a patient has forgotten to dispense a medication at the time that he is supposed to take it, or when optional temperature and/or humidity sensors indicate that the medication is being improperly stored. It will be understood that, depending on the user interface needs of the embodiment, the control switches may be assigned to other functions.

The electronic circuit 2500 may also optionally include alarm devices, such as the buzzer 2530 and/or a vibration device 2532. These alarm devices may be activated by the processor 2502 separately or in unison, to alert a user to a variety of conditions. In some embodiments, the buzzer 2530 may be controlled to produce a variety of different sounds to alert a user to various conditions. For example, one sound may be used to warn the user that he should take a dose of a medication, another sound may be used to warn the user that he is attempting to dispense additional medication before it is safe to take another dose, a further sound may be used to warn the user that the medication in the container is running low, another sound may be used to indicate that the battery is low, and still another sound may be used to indicate to the user that temperature and/or humidity sensors are indicating that the medication is not being properly stored. In some embodiments, the buzzer 2530 may be a small speaker, capable of producing sounds including buzzing noises, speech, musical tones, or other sounds, depending on the message to be conveyed to the user.

The timing of the sounds or vibrations produced by the buzzer 2530 and/or vibration device 2532 may be controlled by the processor 2502 to convey particular meanings or warnings. For example, the processor 2502 may be programmed to use the buzzer 2530 to produce a warning sound at a predetermined time after the solid preparation should have been dispensed. For example, a short beep could be generated every minute during one hour following the time when the solid preparation should have been dispensed. The processor 2502 may be programmed to cease such warnings when the solid preparation has been dispensed through the dispenser.

The processor 2502 may be programmed to use the vibration device 2532 in a similar manner. For example, the vibration device 2532 may be switched on for one second at the time that the solid preparation should be dispensed. This may be repeated, for example, sixty minutes later, if the solid preparation is not dispensed.

In some embodiments, the electronic circuit 2500 may optionally be connected to a blocking mechanism 2534. When activated, the blocking mechanism 2534 prevents the dispenser from dispensing a solid preparation. This can be achieved, for example, by sending electrical signals to a motor or solenoid to move a stopper notch between a locked and an unlocked position, as described above. The blocking mechanism 2534 may be used, for example, to prevent a user from dispensing a further dose of a medication during a time period over which a further dose is not needed or could be dangerous, or from dispensing medication which may have been damage by exposure to temperatures or humidity levels outside of an acceptable range.

In some embodiments, the electronic circuit 2500 may further include additional sensors, such as a humidity sensor 2536 and/or a temperature sensor 2538, positioned in such a way that they are able to detect the humidity and/or temperature of the pills, capsules, or other solid preparations stored in the dispenser device. The humidity sensor 2536 may, for example, be a capacitive humidity sensor, a resistive humidity sensor, a thermal conductivity humidity sensor, or other suitably small, commercially available electronic humidity detection device. Similarly, the temperature sensor 2538 may be a thermistor or other resistance temperature detector, or any other suitably small, commercially available electronic temperature detector. These sensors should be positioned so that they measure the temperature and/or humidity of the pills, capsules, or other solid preparations stored in the container, bottle, or dispenser.

In dispenser embodiments, the electronic circuit 2500 may be configured to fit within a portion of the dispenser mechanism, and is built onto the electronics disc 12, as shown in earlier figures above. The electronic circuit 2500 may also be built into other portions of a medication container or bottle. For example, the electronic circuit 2500 may be built into the lid or the base of a medication bottle. Individual components of the electronic circuit 2500 may be built into other portions of the dispenser, depending on their function. For example, the humidity detector 2536 and temperature detector 2538 may be positioned so that they measure the humidity and/or temperature in the locations where pills, capsules, or other solid preparations are stored, such as the reservoir 5 shown in preceding figures and discussed above.

In addition to the features described above, the electronic circuit 2500 and/or medication container or dispenser may include an identity detection device (not shown). Such an identity detection device may be connected to the electronic circuit 2500 to permit the user of the dispenser or medication container to be identified. An example of such an identity detection device is a fingerprint reader and identifier. The processor 2502 may be programmed to accept signals from such a fingerprint reader (not shown), and to activate the dispenser or allow opening the medication container only when the fingerprint read by the fingerprint reader matches a stored fingerprint. The stored fingerprint may be stored in the memory 2504, or in a memory associated with the fingerprint reader (not shown). Since fingerprints are unique, the fingerprint of the authorized user of the device may be stored, so that only the authorized user of the device is able to activate the dispenser and to dispense a solid preparation. Other identity detection devices could also be used, including other (preferably small/portable) biometric devices, or security measures such as requiring the user to enter a combination or a personal identification number (PIN).

By adding such an identity detection device to the electronic circuit 2500, an identity function may be implemented for the dispenser or medication container. This identity function makes it possible that only an authorized or intended user, such as the patient or a caregiver, can activate the dispenser or open the medication container. Using this feature, the solid preparation could not be accessed, for example, by a child who finds the device. Additionally, the identity function may reduce the risk of taking the wrong medication, for example if there are several such dispensers or containers being used by different people in a single household.

Further, the electronic circuit 2500 may be connected to an RFID reader (not shown) in the dispenser. Some medication containers (not shown) may be equipped with RFID chips (not shown) that can contain information on the medication in the container. Such RFID chips may be placed on or built into the container when the container is manufactured, or at a later time, such as when a pharmacist provides the container containing medication to the patient. The RFID chip in such a container may be a standard MIFARE RFID chip, or any other type of RFID chip or tag. A drug manufacturer, physician, and/or pharmacist may store information on the RFID chip. For example, the RFID chip may include the date and time of packing a medication in the container, the content of the container, the drug type and number of pills, the expiration date of the medication, a unique identification number, patient medication intake times, length of the course of treatment, pharmacist license number, prescribing physician license number, proper storage temperature and humidity ranges, and/or other information pertaining to the solid preparation contained in the container. In some embodiments, similar information may be stored in the memory of the dispenser or other device rather than in an RFID chip, for example by the pharmacist who dispenses the medication, a physician, or a patient.

The RFID reader may be used to read this information from the RFID chip attached to the container when the dispenser or other device (e.g. a lid) containing the electronic circuitry 2500 is attached to the container. The information can then optionally be stored in the memory 2504, and used by the processor 2502 for a variety of purposes. For example, if the dispenser or medication container includes a display, such as the display 2514, the information read by the RFID reader may be displayed. This can reduce the risk of taking the wrong medication or medication that has passed its "use by" date. The risk of taking the wrong medication may be especially pronounced when a patient needs to take two or more types of medication. When an RFID reader in the dispenser or medication container is used with an RFID chip on the container, the patient is able to read on the display which of his medications is contained in the container. This may be particularly useful when the labelling of the container has faded, for example due to frequent use or contact with water or solvents. The processor 2502 may use the information read from an RFID chip on the container for purposes such as displaying the drug contained in the container, determining when the container is almost empty (based on pill count), automatically programming the times that the solid preparation should be dispensed or accessed so that the processor 2502 may generate alarms at the proper times, producing a warning when a medication has expired or has been stored at an unacceptable temperature and/or humidity level, preventing a user from dispensing or accessing the solid preparation at the wrong times, after it has expired, after a course of treatment has been completed, if improper temperature and/or humidity conditions may have affected the medication, and other uses for such information.

Additionally, in some embodiments, the RFID reader may also store information back into the RFID chip on the container. This means that compliance information may be available in the container chip when it is returned to the pharmacist, for example for a refill.

Referring now to FIG. 25, a system 2600 for communicating with a dispenser or medication container 2601 is described. A docking station 2602 is used for electronic data communication and electronic data transfer between the dispenser or medication container and a computer (not shown) or other communication device (not shown). Additionally, in some embodiments, the docking station 2602 may be used to recharge a rechargeable battery in the dispenser or medication container.

In some embodiments, the docking station 2602 may include a wired connection 2604, such as a USB connection or other wired connection for transferring data between the docking station 2602 and a computer or other communication device. In some embodiments, the docking station 2602 may include a wireless communication device (not shown) to allow the docking station 2602 to communicate via a wireless connection, such as through a cellular network, a wireless wide area network, or a wireless local area network. The docking station may be powered using an AC mains adapter 2606, or through power received over the wired connection 2604.

The docking station 2602 is also equipped with a electronic reader-writer device (described below), for reading and writing data from the dispenser or medication container. In some embodiments, where the dispenser or medication container is able to communicate directly with a wide area network or cellular network, or where the communication is handled by a portable reader, such as a mobile phone equipped with an NFC reader, the docking station 2602 may not be needed for the dispenser or medication container to communicate its data.

FIG. 26 shows a block diagram of an electronic reader-writer device 2700 suitable for use in the docking station 2602 of FIG. 25. The reader-writer device 2700 includes a second transceiver 2702 with a second antenna 2704 for communicating with the first transceiver 2510 in the dispenser, as shown in FIG. 24. When used with the reader-writer device 2700 in a docking station, the dispenser or medication container may preferably use a low power, short range communication technology, such as Near Field Communication (NFC), Bluetooth, or ZigBee. Other communications technologies suitable for longer range wireless communications may also be used, such as WiFi or other wireless local area network (WLAN) technology. Of course, the communication technology used by the reader-writer should be compatible with the communication technology used by the dispenser or medication container. Alternatively, a physical electrical connection between the dispenser or medication container and the docking station could be used, assuming that the dispenser or medication container includes an appropriate interface. For example, if the dispenser has a USB interface, it may be possible to connect it to the docking station (or directly to a USP-equipped external computer) using the USB interface. A physical interface, such as a USB interface, may also be useful for charging a rechargeable battery in the dispenser.

The reader-writer device 2700 also may include a wired connection interface 2706. The wired connection interface 2706 may be, for example, a USB interface through which the reader-writer device connects the docking station to an external computer system. Other types of wired connections, such as a serial connection or a wired Ethernet connection could also be used.

The reader-writer device 2700 may be powered from an AC adapter (not shown) through a voltage regulator 2708. Alternatively power may be received from other sources, such as through the wired connection interface 2706.

Once the data are transferred from the dispenser or medication container to an external computer (through a docking station, such as the docking station 2602, shown in FIG. 25, when the dispenser is unable to communicate directly with the external computer), the external computer can transfer the data to a remote computer via a wide area network, such as the Internet. The dispenser or medication container may also receive data, such as revised expiration date data based on temperature and/or humidity readings, or proper temperature and/or humidity ranges for storage of the medication via a wide area network through an external computer (and, possibly a docking station). Further, programming or instructions for the electronic circuit 2500 of the dispenser, as shown in FIG. 24, may be sent from a computer at a remote location, and communicated to the dispenser via the Internet or other wide area network. The remote computer may, for example, be accessible by a physician, pharmacist, or other medical professional who is overseeing the therapy compliance of the patient who is using the dispenser or medication container. It will be understood that in some embodiments, where the dispenser or medication container includes wide-area networking or cellular communication capabilities, the dispenser may be able to connect to the Internet and/or the remote computer system without using an external computer or docking station to establish the connection. It will also be understood that in some embodiments, a mobile device, such as an NFC-equipped mobile telephone may be used to communicate between the remote computer and the dispenser.

Such a system is shown in FIG. 27. The system 2800 of FIG. 27 includes one or more dispensers (or medication containers) 2802, which include the electronic circuitry 2500 as shown in FIG. 24. For purposes of illustration, these dispensers include NFC communication circuitry, which allows them to transfer data between a dispenser 2802 and an NFC-equipped mobile telephone 2804. The NFC-equipped telephone 2804 can wirelessly communicate via a wide area network 2806, such as a cellular communication network or the Internet with a remote database 2808, which collects and stores information from the dispenser(s) 2802. The remote database 2808 can be accessed (through the wide area network 2806 or a different wide area network) by a remote computer 2810, which may also remotely send instructions to the dispenser(s) 2802 through the wide area network 2806 and the mobile telephone 2804.

It will be understood that the communication path may be somewhat different, depending on the technology used. For example, if no NFC-equipped mobile phone is available, the dispenser may use a docking station (not shown) connected to a computer (not shown) to communicate with the remote database 2808 and/or the remote computer 2810. Alternatively, in some embodiments, the dispenser may be able to directly connect to the wide area network, and communicate with the remote database 2808 and/or the remote computer 2810 without using an NFC-equipped mobile telephone or a docking station.

As can be seen in FIG. 27, the therapy compliance monitoring and communication means provided can be mobile. The dispenser 2802 is arranged for monitoring the therapy compliance of a patient, and for remotely allowing or disabling the dispensing of a solid preparation, to help ensure therapy compliance. Wired and/or wireless communications can be used to report therapy compliance, and the temperature and/or humidity at which medications are being stored to the remote computer 2810, which may be used by a physician, pharmacist, or other medical caregivers to monitor compliance and other conditions, such as temperature and/or humidity of the medication. Additionally, administration of therapy may be controlled or adjusted from the remote computer 2810, depending on the information received. Further, as can be seen, in addition to the Internet, other communication technologies may be used in the remote surveillance and control of therapy compliance, including mobile platforms, such as the mobile telephone 2804, and the like.

When a container with a solid preparation is issued by a pharmacist, the dispenser 2802 or other device containing the electronic circuitry and temperature and/or humidity detectors is put in place on the container. Alternatively, the circuitry and sensors may be built into the container into which the pharmacist places the medication. The dispenser 2802 has a built-in clock/calendar so that when a solid preparation, such as a pill or tablet is dispensed, the date and time of this event are stored in a memory in the dispenser 2802. Similarly, the times of recording temperature and or humidity readings can be stored. In dispenser embodiments, the dispenser 2802 may optionally be programmed so that the solid preparation may only be dispensed at pre-programmed times, depending on the medication prescribed, and the instructions of the physician and/or pharmacist. This may prevent a patient from taking too many doses, since the dispenser 2802 is blocked after a dosage is taken, and will only dispense a further dose when the next dosage should be taken. It should also be noted that this option of programming the dispenser provides the opportunity to register and regulate a combination therapy, whereby more than one type of medication must be taken, as will be described in greater detail below.

Next, the date and time stamp at which a dose was dispensed, and/or other information, such as temperature and/or humidity data are transferred over the wide area network, which may be a mobile telephone network, such as GSM or GPRS, to the patient's record in the remote database 2808. As shown in the figure, in some embodiments, this transfer may be accomplished by reading the data from the dispenser using a Near Field Communication (NFC) mobile phone 2804, or by using another gateway for conversion of data from NFC or Bluetooth devices into SMS and GPRS data. It will be understood that other communication options, as described above are also possible. Other data collected by the dispenser may also be transferred along with the compliance data, or as separate transmissions. For example, data concerning the temperature and humidity of the stored medication may be transferred. These data may indicate whether the pills, capsules, or other solid preparations are being stored in appropriate conditions. This information may be used to send the patient and/or the pharmacist or physician a warning if the medication is being stored at an inappropriate temperature or humidity. This data could also be used, for example, to dynamically adjust the expiration date of a medication, depending on its storage conditions, or to prevent a patient from taking medications which could become dangerous if stored for a period of time in an inappropriate manner. Other information, such as the battery status may also be transferred. This data may, for example, be used to warn the patient or pharmacist if a non-rechargeable battery in the dispenser device will need to be replaced.

The patient record in the database 2808 may contain various kinds of patient information, including the therapy compliance records for the patient received from one or more dispensers. This information can be securely accessed by physicians, pharmacists, or other authorized medical caregivers from a remote computer 2810 over a wide area network, such as the Internet. The compliance data may be correlated and analyzed in the remote database 2808 or on the remote computer 2810, and if mal-compliance or noncompliance are detected, the patient can be warned, for example via an SMS service or the like. In some embodiments, when noncompliance or mal-compliance are detected, a call centre, pharmacist, and/or care organization may receive an instruction to call the patient to discuss his mal- or noncompliance.

In some embodiments, a dispenser may also communicate with another dispenser, either directly, through a docking station, or through a network. An advantage of such a dispenser is that it is possible to regulate an order in which two or more medications are taken. For example, in AIDS treatment, a combination of drugs may be prescribed, which need to be taken in a strict order and according to a strict time schedule. For example, the prescription schedule can specify that a first medication should be taken first, followed within one hour by a second medication. If the patient forgets that he has already taken the required dosage of the first medication, he may try to "correct" this by taking another dose of the first medication. Such noncompliance can have serious effects on the health of the patient and on the effectiveness of the treatment.

By communicating with each other, the dispensers can reduce this problem. Using the above-described example, a first dispenser for a container containing the first medication can block further dispensing of the first medication until it receives a communication indicating that a second dispenser for a container containing the second medication has dispensed a dose of the second medication. Thus, a new dose of the first medication can only be taken after the required dose of the second medication has been taken. The time for taking the second medication can be set by the second dispenser receiving a communication indicating that the first medication has been dispensed by the first dispenser, causing the second dispenser to set a buzzer or other alarm feature to provide a warning one hour later that the second medication should be taken. By use of dispensers that are able to communicate with each other, according to an embodiment of the invention, a strict medication regime can be followed with reduced effort by the patient and with an increased rate of compliance.

It should be noted that in accordance with various embodiments of the invention, communication between the dispensers can be achieved directly between the dispensers, or via an indirect method. For example, the dispensers may communicate through a base station, or through a wireless network. Also, the dispensers could communicate indirectly through a database, such as the remote database 2808 shown in FIG. 28, or through another computer or communication device that receives and sends communications to dispensers in accordance with various embodiments of the invention.

In an embodiment of a system such as is shown in FIG. 27, in which the dispenser communicates with a mobile phone, the mobile phone may handle various functions of the system, such as alarming functions, displaying compliance and other information to a patient, interacting with the user to send commands to the dispenser, and/or facilitating communications between a patient and pharmacist and/or physician. For example, instead of generating a beeping noise from the dispenser when it is time to take medication, the dispenser may cause the mobile phone with which it communicates to generate a noise or send a message, warning the patient (i.e., the owner of the mobile phone) that it is time to take medication. As a further example, the dispenser may instruct the mobile phone to warn the patient that the medication is almost depleted. When this warning is received the mobile phone may be configured (e.g., via special purpose software) to warn the patient, provide an option to automatically order refill medication, and/or tie into other services, such as mapping services, to direct the patient to a nearby pharmacy. If it is determined that the patient's compliance is poor, or that the medication is not having its intended effect (e.g., due to data sent from physiological monitoring equipment (not shown)), the database 2808 or the medication dispenser may instruct the mobile phone to warn the user, and may provide options to call a physician or schedule an appointment. Warnings provided by mobile phones can use a wide variety of sounds available on mobile phones, or can be delivered via voice or text message. Communication between the mobile phone and the database can be handled using the mobile phone's communication capabilities, e.g., through GPRS (General Packet Radio Service) or other mobile data communications services. Because of the widespread use and ownership of mobile phones and mobile phone services, a mobile phone may provide a widely-available interface to medication dispensing systems and to related services.

At present, an increasing number of mobile phones are able to communicate wirelessly with devices such as the medication dispenser using communications devices and protocols in accordance with the NFC (Near Field Communication) standard. In accordance with the invention, the data collected by a medication dispenser may be communicated using a specialized Record Type Definition within the Near Field Communication Data Exchange Format. An example embodiment of such a Record Type Definition is shown in FIG. 28.

As seen in FIG. 28, a dispenser datastream 2820 includes the following fields:

1. Data length field 2822, for specifying the number of bytes of information in the record.
2. RTD (Record Type Definition) indication number field 2824, which is used to identify the RTD of the record as a dispenser datastream record.
3. URL of the database server field 2825, used for specifying the URL (Uniform Resource Locator) of the database server where the patient and/or compliance data are stored.
4. Dispenser ID field 2826, used for a unique identifier for each dispenser, including a manufacturer ID, a date of manufacturing, and a code for the place of manufacturing.
5. Device type ID field 2828, used to specify information identifying the type of the dispenser.
6. Drug ID of the content field 2830, used to specify information identifying the drug contained in the dispenser.
7. Patient ID field 2832, used to specify information identifying the patient (e.g., a patient ID number).
8. Pharmacist ID Hand-out field 2834, used for information identifying the pharmacist who handed out the dispenser and/or the drug contained in the dispenser.
9. Pharmacist ID Hand-in field 2836, used for information identifying the pharmacist to whom the dispenser was handed in, and/or to whom the dispenser should be handed in.
10. Date of packing field 2838, used for the date on which the dispenser was last filled. Alternatively, this field can be used to indicate the expiration date of the drugs in the dispenser. In some embodiments, this field may contain both the date of packing, and the expiration date.
11. Number of pills packed field 2840, used for the number of pills originally placed in the dispenser. In alternative embodiments, in which a blister pack is used, this field may indicate the number of blisters that are filled with pills or capsules. In alternative embodiments, such as liquid dispensers, injectables, or inhalers, this field may be used to indicate the number of doses, amount of liquid, etc., as appropriate for the type of dispenser.
12. hand-out time of the dispenser field 2842, used to indicate the time (and date) at which the dispenser was handed out.
13. hand-in time of the dispenser field 2844, used to indicate the time (and date) at which the dispenser was handed in or returned.
14. Number of times information read field 2846, used to indicate the number of times that information has been read from the dispenser by the mobile phone.
15. dispenser date and time field 2848, indicating the current date and time according to the dispenser clock.
16. phone date and time field 2850, indicating the date and time of the clock on the telephone that read the data.
17. Battery condition field 2852, indicating the state of the battery.
18. Temperature range field 2854, indicating the minimum and maximum temperature over the time from the hand-out time to the current time (if the current time is prior to the hand-in time) and/or the hand-in time (if the current time is after the hand-in time).
19. Temperature field 2856, indicating the current temperature measurement.
20. Humidity range field 2858, indicating the minimum and maximum humidity over the time from the hand-out time to the current time and/or the hand-in time.

21. Humidity field 2860, indicating the current humidity measurement.

22. Lock time field 2862, indicating a time at which the dispenser was locked, such that no dose may be dispensed. In some embodiments, this field may be used to indicate a time over which the dispenser is to remain locked.

23. Unlock time field 2864, indicating a time at which the dispenser was (or is to be) unlocked. In some embodiments, this field may be used to indicate a period of time over which the dispenser should be unlocked, such that a dose can be dispensed.

24. Number of doses dispensed field 2866, indicating the number of doses that have been dispensed. For example, in a pill dispenser, such as is shown above, this would indicate the number of pills that have been dispensed. In a liquid dispenser, it would indicate the number of doses of the liquid that have been dispensed.

25. Dosage dates and times field 2868, indicating the dates and times at which doses were dispensed. Generally, this field may include the date and time for each of the doses that have been dispensed since the hand-out time of the dispenser. In some embodiments, this may have an upper limit, depending on the memory available in the dispenser. For example, in some embodiments, this field may provide the date and time for up to the last 200 doses that were dispensed.

26. Check sum field 2870, containing a check sum verifying that no data have been lost or altered. In some embodiments, this field may contain a cyclic redundancy check code for the rest of the record.

It will be understood that the record type definition discussed above could be varied, depending on the dispenser and sensors available. For example, in embodiments where temperature and/or humidity are not measured, the fields for these measurements could either be left empty, or a slightly varied record type definition omitting these fields could be used. It will also be recognized that the order and exact content of the fields may be altered. The content of the record can be sent between the dispenser and the mobile phone and/or between the mobile phone and database in an encrypted form. It will further be recognized that although the record type definition has been described as a Near Field Communication record type definition, other short-range communications systems, such as Bluetooth, could be used, and a similar record type definition (altered to fit the requirements of the communication system) could be used in such systems.

Thus, in accordance with embodiments of the invention, a medication container is provided. The medication container may be equipped with an electronic temperature sensor and/or an electronic humidity sensor positioned within the container such that the temperature and/or humidity within the container may be measured. The medication container is further equipped with electronic circuitry that receives readings from the electronic temperature sensor and/or the electronic humidity sensor, and stores and/or transmits the readings to an external device. In some embodiments, the medication container is a dispenser.

The temperature sensor in any of the preceding embodiments may be a thermistor or other resistance temperature detector. The humidity sensor in any of the preceding embodiments may be a capacitive humidity sensor, a resistive humidity sensor, or a thermal conductivity humidity sensor.

The medication container of any of the preceding embodiments may include an alarm device, such as a buzzer or vibration device. An alarm may be produced when the temperature sensor and/or the humidity sensor indicates that the medication contained in the container is being stored at a temperature and/or humidity that is outside of an acceptable temperature and/or humidity range. The acceptable temperature and/or humidity range will depend on the medication stored in the container.

In the medication container of any of the preceding embodiments, the circuitry may receive information and/or commands from an external source. This information may include an acceptable temperature and/or humidity range for the medication contained in the medication container and/or an expiration date for the medication in the container calculated based on the temperature and/or humidity readings sent to the external device. The commands received from the external source may include a command to alert the user that the temperature and or humidity readings sent to the external device are outside of an acceptable temperature and/or humidity range. Additionally, the medication container may include a blocking device that prevents access to the medication stored in the container, and the commands received from the external source may include a command to activate the blocking device to prevent access to the medication if the medication has been stored at a temperature and/or humidity outside of an acceptable temperature and/or humidity range.

While the invention has been discussed in terms of a pill dispenser, there are other types of medication dispensers or containers that could be used in accordance with the electronic and compliance monitoring aspects of the invention. The systems described with reference to FIGS. 24-28 above could be used (with slight modification), for example, with liquid dispensers, inhalers, injectable delivery devices (i.e., a needle and syringe or an infusion control pump), and/or blister packs.

Figure 29B:
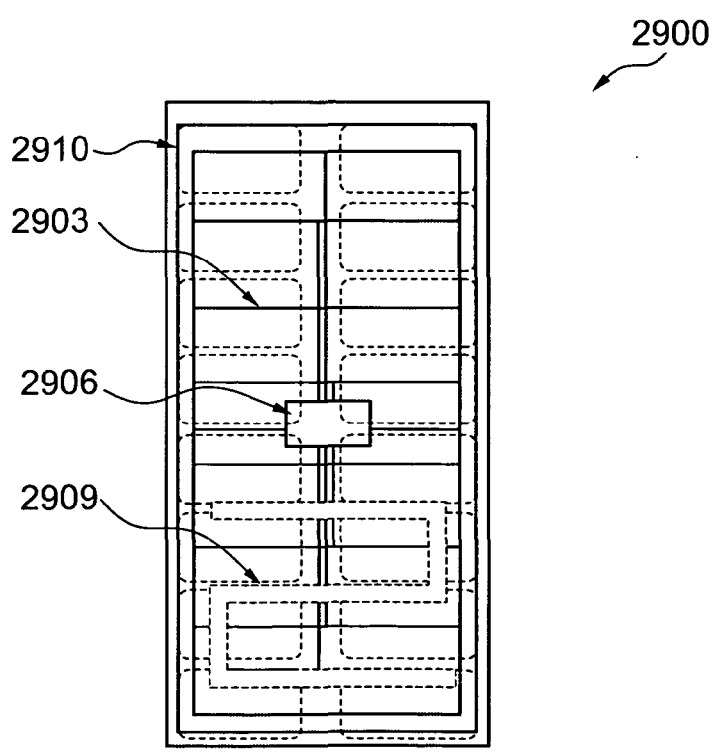

FIGS. 29A and B show an example of a blister pack that could be used in such a system. FIG. 29A illustrates the front side of a blister pack 2900 with compartments 2904, which are filled with pills 2907 which can be expelled from the blister via openings 2905 in the film 2902, which openings are sealed with foil 2901. FIG. 29B illustrates the rear side of such a blister pack whereby the foil 2901 includes a pattern of conductive tracks 2903 that have been printed in such a way that when the pills 2907 are expelled via the openings 2905 the conductive track under the opening is broken and this break in the conductive track is detected by the integrated circuit 2906. In some embodiments, to reduce the costs associated with such a blister pack, the conductive tracks 2903 may be a polymer-based electronic circuit, printed directly on the film 2902. Similarly, the integrated circuit 2906 may be implemented as a polymer-based printed electronic device in some embodiments. Where wireless communication with the blister pack is desired, an antenna (not shown) may also be printed on the film 2902 and/or foil 2901.

Figure 30B:
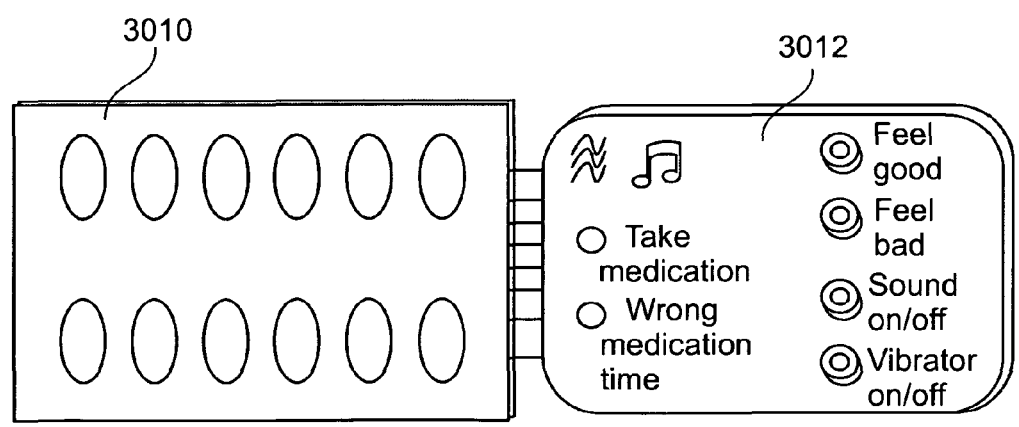

FIGS. 30A and 30B show an alternative embodiment of a blister pack that can be used with a system such as is described above. In the blister pack 30A, a label 3002 including conductive tracks 3004 has been placed over the foil (not shown) of a conventional blister pack, such that when a pill or other solid preparation is removed from the blister pack, one of the conductive tracks 3004 will be broken. The label 3002 includes an adhesive part 3006 that is placed over the conventional blister pack, and a contact part 3008 that is used to connect the conductive tracks 3004 to an electronics package, which may be removable. FIG. 30B shows the front of the conventional blister pack 3010, in which an electronic package 3012 has been connected to the contact part 3008. The electronic package 3012 may contain circuitry similar to that shown above with reference to FIG. 24, and may allow conventional blister packs to be used in a system such as is described above with reference to FIGS. 25-28. It will, of course, be understood that the electronics are not exactly the same as are illustrated in FIG. 24. For example, there is no need for an optical detector to detect pills being dispensed. Instead, the conductive tracks 3004 are connected to the processor to determine when a pill or other solid preparation has been removed from the blister pack. Similarly, since the humidity within the individual blisters is easily controllable, there may be no need for a humidity detector.

Similar systems may be used with other types of medication dispensers. For example, for liquid medications, a dispenser that provides a uniform dose could be used in connection with electronics similar to those shown in FIG. 24, and a system similar to that shown in FIGS. 25-28. Liquid levels could be determined, for example, using ultrasound. Other medication dispenser types, such as inhalers (the contents of which might be measured using a pressure sensor), or dispensers for injectables could also be used with such a system.

Other variations to the disclosed embodiments can be understood and effected by those skilled in the art and practicing the claimed invention, from the studying of the drawings, the disclosure, and the appendant claims. In the claims the word comprising does not exclude other elements or steps and the indefinite article "a" or "an" does not exclude a plurality.

The invention claimed is:

1. A dispenser for dispensing capsules or pills in a unit dose manner, the dispenser comprising:
    a reservoir having a plurality of compartments, wherein at least one compartment of the plurality of compartments is able to store a plurality of the capsules or pills;
    a positioning disc having a plurality of exit orifices;
    a guiding member rotatably arranged between the reservoir and the positioning disc and respectively connecting a compartment with a dedicated exit orifice in dispensing communication by accomplishing a rotary/rotational step;
    an actuator which is shaped and arranged for releasably stopping the guiding member when the guiding member accomplishes the rotary/rotational step to bring the compartment of the reservoir in dispensing communication with the dedicated exit orifice; and
    a cover and a housing, the cover providing a releasing member which comes into load transmitting contact with the actuator when the cover is seated on the housing and which moves the actuator out of its stoppage position engaging a stopper member.

2. A dispenser according to claim 1, wherein at least one of the actuator and the guiding member is part of a driving mechanism which is releasably blocked by the actuator to stop further rotary/rotational motion when the driving mechanism reaches an index position indicating the dispensing communication.

3. A dispenser according to claim 1, wherein the reservoir and the positioning disc comprise a correspondingly arranged number and configuration of compartments, each having an open end, and exit orifices, wherein the pattern of the open ends and the exit orifices are dislocated in respect to each other in a circumferential direction.

4. A dispenser according to claim 1, wherein the actuator is pivotable with respect to another part of the dispenser.

5. A dispenser according to claim 1, wherein the actuator comprises a stopper notch and a guiding notch, wherein the guiding notch interacts with a stopper member for carrying out a radially inwardly directed rotational movement of the stopper notch during each rotary/rotational step of the part respecting which the actuator is pivotable to bring the stopper notch into a blocking contact with another stopper member afterward for accomplishing the rotary/rotational step.

6. A dispenser according to claim 1, wherein the cover forms a moisture tight seal with the housing.

7. A dispenser according to claim 1, wherein at least one of the parts of the dispenser is composed of a polymer.

8. A dispenser according to claim 1, wherein the guiding member comprises a connecting channel, and wherein the connecting channel is of such a height that it can contain only one single dose unit of a solid preparation, which makes it possible to dispense one single dose unit during each rotary/rotational step.

9. A dispenser according to claim 8, the dispenser comprising an indexing wheel, wherein:
    the guiding member is at least a part of the indexing wheel,
    the indexing wheel comprises a receiving opening and a dispensing opening, and
    the receiving opening and the dispensing opening are connected by the connecting channel.

10. A dispenser according to claim 1, wherein the dispenser is arranged in such a way, that by accomplishing a rotary/rotational step a first pill or capsule is released from a first compartment into the guiding member and simultaneously a second pill or capsule from a second compartment is dispensed from the guiding member.

11. A dispenser according to claim 1, wherein the compartments are in the form of cylindrical tubes.

12. A dispenser according to claim 11, wherein the cylindrical tubes are adapted to house more than one capsule per tube.

13. A dispenser according to claim 1, wherein at least one of the parts of the dispenser is composed of a desiccant entrained polymer.

14. A dispenser for dispensing capsules or pills in a unit dose manner, the dispenser comprising:
    a reservoir having a plurality of compartments, wherein at least one compartment of the plurality of compartments is able to store a plurality of the capsules or pills,
    a positioning disc having at least one exit orifice,
    a guiding member for respectively connecting one compartment with the at least one exit orifice, wherein at least one of the reservoir and the positioning disc is rotatably arranged in respect to the respective other components,
    an actuator shaped and arranged for releasably assuring a stoppage of the at least one rotatably arranged component when the at least one rotatably arranged component is rotated to bring a compartment of the reservoir in dispensing communication with the at least one exit orifice, and
    a cover and a housing, the cover providing a releasing member which comes into load transmitting contact with the actuator when the cover is seated on the housing and which moves the actuator out of its stoppage position engaging a stopper member, and wherein the cover forms a moisture tight seal with the housing.

15. A method for dispensing in a unit dose manner a solid preparation having the spatial dimensions of a capsule or pill; comprising:
    providing a dispenser comprising:
        a reservoir having at least a first compartment able to store the first solid preparation,
        a positioning disc having a plurality of exit orifices, and
        a guiding member being rotatably arranged in between the reservoir and the positioning disc and respectively connecting the first compartment with a first dedicated exit orifice in dispensing communication by accomplishing a rotary/rotational step;

a cover and a housing, the cover providing a releasing member which comes into load transmitting contact with an actuator of the dispenser when the cover is seated on the housing and which moves the actuator out of its stoppage position engaging a stopper member, and wherein the cover forms a moisture tight seal with the housing;

providing a first solid preparation in the first compartment of the reservoir; and rotating the guiding member to a first dispensing position to connect the first compartment with the first dedicated exit orifice in dispensing communication.

16. The method according to claim 15, in which the provided dispenser further comprises a second compartment in the reservoir able to store a second solid preparation, and a second compartment in the guiding member configured for connecting with a second dedicated exit orifice in dispensing communication by accomplishing a rotary/rotational step;

and the method further comprises:

providing a second solid preparation in the second compartment of the reservoir; and rotating the guiding member to a second dispensing position to connect the second compartment with the second dedicated exit orifice in dispensing communication.

17. A dispenser for dispensing capsules or pills in a unit dose manner, the dispenser comprising:

a reservoir having a plurality of compartments, wherein at least one compartment of the plurality of compartments is able to store a plurality of the capsules or pills;

a positioning disc having a plurality of exit orifices;

a guiding member rotatably arranged between the reservoir and the positioning disc and respectively connecting a compartment with a dedicated exit orifice in dispensing communication by accomplishing a rotary/rotational step, and wherein the guiding member comprises a connecting channel, the connecting channel being of such a height that it can contain only one single dose unit of a solid preparation, which makes it possible to dispense one single dose unit during each rotary/rotational step;

an actuator which is shaped and arranged for releasably stopping the guiding member when the guiding member accomplishes the rotary/rotational step to bring the compartment of the reservoir in dispensing communication with the dedicated exit orifice;

a cover and a housing, the cover providing a releasing member which comes into load transmitting contact with the actuator when the cover is seated on the housing and which moves the actuator out of its stoppage position engaging a stopper member; and an indexing wheel, wherein the guiding member is at least a part of the indexing wheel, the indexing wheel comprises a receiving opening and a dispensing opening, the receiving opening and the dispensing opening are connected by the connecting channel, and the receiving opening and the dispensing opening are of a double-hole pattern comprising two through holes, wherein the dispenser is adapted in such a way, that by accomplishing a rotary/rotational step only one of the through holes is connected to an open end of a compartment, respectively, whereas the other one is simultaneously connected to an exit orifice.

* * * * *